US009366621B2

United States Patent
Howell et al.

(10) Patent No.: US 9,366,621 B2
(45) Date of Patent: Jun. 14, 2016

(54) IN-FURNACE RETRO-REFLECTORS WITH STEERABLE TUNABLE DIODE LASER ABSORPTION SPECTROMETER

(71) Applicant: Zolo Technologies, Inc., Boulder, CO (US)

(72) Inventors: Jim Howell, Louisville, CO (US); Bernard Patrick Masterson, Louisville, CO (US); Rod Harris, Fort Collins, CO (US); David Giltner, Boulder, CO (US); Atilio Jobson, Boulder, CO (US); Michael John Estes, Longmont, CO (US); Andrew D. Sappey, Lakewood, CO (US)

(73) Assignee: Zolo Technologies, Inc., Louisville, CO (US)

( * ) Notice: Subject to any disclaimer, the term of this patent is extended or adjusted under 35 U.S.C. 154(b) by 142 days.

(21) Appl. No.: 14/395,037

(22) PCT Filed: Mar. 15, 2013

(86) PCT No.: PCT/US2013/032479
§ 371 (c)(1),
(2) Date: Oct. 16, 2014

(87) PCT Pub. No.: WO2013/158311
PCT Pub. Date: Oct. 24, 2013

(65) Prior Publication Data
US 2015/0109618 A1 Apr. 23, 2015

Related U.S. Application Data

(60) Provisional application No. 61/635,733, filed on Apr. 19, 2012.

(51) Int. Cl.
*G01N 21/55* (2014.01)
*G01N 21/39* (2006.01)
(Continued)

(52) U.S. Cl.
CPC ............. *G01N 21/39* (2013.01); *F23M 11/045* (2013.01); *F23M 20/00* (2015.01); *F23N 5/082* (2013.01);
(Continued)

(58) Field of Classification Search
CPC ....... G01M 15/14; G01N 21/25; G01N 21/39; G01N 21/00; F02C 7/22; F23N 5/08; F24H 9/20
USPC ................... 356/445, 43, 432, 326, 437, 342; 422/78
See application file for complete search history.

(56) References Cited

U.S. PATENT DOCUMENTS 2,841,122 A 7/1958 Tollow
2,930,893 A 3/1960 Carpenter
(Continued)

FOREIGN PATENT DOCUMENTS

CN 1163665 A 10/1997
CN 1343873 4/2002
(Continued)

OTHER PUBLICATIONS

Allen (1998) "Diode laser absorption sensors for gas-dynamic and combustion flows" Measuring Science and Technology 9:5450562.
(Continued)

*Primary Examiner* — Tarifur Chowdhury
*Assistant Examiner* — Isiaka Akanbi
(74) *Attorney, Agent, or Firm* — Swanson & Bratschun, L.L.C.

(57) ABSTRACT

A method of monitoring combustion properties in an interior of a furnace is described. A beam of light is projected through a pitch optic including a pitch collimating lens residing outside the boiler interior. The pitch collimating lens projects the beam through a penetration into the boiler interior. The beam of light projected by the pitch collimating lens is reflected from at least one in-furnace retro-reflector, and received with a catch optic substantially identical to the pitch optic residing outside the boiler interior. The pitch optic and the catch optic may be embodied in the same pitch/catch optic. The pitch collimating lens may also be steered toward another of the at least one in-furnace retro-reflectors. Combustion properties may be calculated for each retro-reflector based on retro-reflector zones within the furnace.

20 Claims, 12 Drawing Sheets

(51) Int. Cl.

| | | |
|---|---|---|
| *G01N 21/84* | (2006.01) | |
| *F23M 11/04* | (2006.01) | |
| *F23N 5/08* | (2006.01) | |
| *F23M 20/00* | (2014.01) | |
| *G01J 3/02* | (2006.01) | |
| *G02B 5/122* | (2006.01) | |
| *G01J 3/42* | (2006.01) | |

(52) U.S. Cl.
CPC ............ *G01N 21/84* (2013.01); *F23N 2029/00* (2013.01); *F23N 2900/05005* (2013.01); *G01J 3/021* (2013.01); *G01J 3/0289* (2013.01); *G01J 3/42* (2013.01); *G01N 2021/399* (2013.01); *G01N 2201/0612* (2013.01); *G02B 5/122* (2013.01)

(56) References Cited

U.S. PATENT DOCUMENTS

| | | | |
|---|---|---|---|
| 3,754,533 | A | 8/1973 | Franzmann |
| 3,778,170 | A | 12/1973 | Howell et al. |
| 4,011,403 | A | 3/1977 | Epstein et al. |
| 4,028,081 | A | 6/1977 | Marcatili |
| 4,037,113 | A | 7/1977 | Moore |
| 4,305,640 | A | 12/1981 | Cullis et al. |
| 4,360,372 | A | 11/1982 | Maciejko et al. |
| 4,432,286 | A | 2/1984 | Witte |
| 4,573,761 | A | 3/1986 | McLachlan et al. |
| 4,659,195 | A | 4/1987 | D'Amelio et al. |
| 4,672,198 | A | 6/1987 | Presby |
| 4,712,888 | A | 12/1987 | Brooks |
| 4,790,652 | A | 12/1988 | Uneus |
| 4,895,421 | A | 1/1990 | Kim et al. |
| 4,915,468 | A | 4/1990 | Kim et al. |
| 4,980,763 | A | 12/1990 | Lia |
| 4,989,979 | A | 2/1991 | Buckman |
| 5,030,000 | A | 7/1991 | Kanda |
| 5,042,905 | A | 8/1991 | Anjan |
| 5,068,515 | A | 11/1991 | van den Bergh et al. |
| 5,291,013 | A | 3/1994 | Nafarrate et al. |
| 5,317,165 | A | 5/1994 | Montagna |
| 5,396,506 | A | 3/1995 | Ball |
| 5,418,881 | A | 5/1995 | Hart, Jr. et al. |
| 5,436,444 | A | 7/1995 | Rawson |
| 5,445,964 | A * | 8/1995 | Lee .................... G01N 21/39 250/343 |
| 5,448,071 | A | 9/1995 | Mccaul et al. |
| 5,468,239 | A | 11/1995 | Tanner |
| 5,477,323 | A | 12/1995 | Andrews et al. |
| 5,506,721 | A | 4/1996 | Hikami et al. |
| 5,515,158 | A | 5/1996 | Heineck |
| 5,553,179 | A | 9/1996 | Cryan et al. |
| 5,592,217 | A | 1/1997 | Hirvonen |
| 5,598,264 | A | 1/1997 | Failes |
| 5,621,213 | A | 4/1997 | Barshad |
| 5,627,934 | A | 5/1997 | Muhs |
| 5,701,376 | A | 12/1997 | Shirasaki |
| 5,717,209 | A | 2/1998 | Bigman et al. |
| 5,717,450 | A | 2/1998 | Hutt et al. |
| 5,732,166 | A | 3/1998 | Hamann et al. |
| 5,742,715 | A | 4/1998 | Boehlke et al. |
| 5,748,325 | A | 5/1998 | Tulip |
| 5,774,610 | A | 6/1998 | O'Rourke |
| 5,798,840 | A | 8/1998 | Beiting |
| 5,802,222 | A | 9/1998 | Rasch et al. |
| 5,805,318 | A | 9/1998 | Rabinovich et al. |
| 5,813,767 | A | 9/1998 | Calabro et al. |
| 5,828,797 | A | 10/1998 | Minott |
| 5,841,546 | A | 11/1998 | Carangelo et al. |
| 5,841,915 | A | 11/1998 | Rabinovich et al. |
| 5,930,029 | A | 7/1999 | Mehuys |
| 5,933,000 | A | 8/1999 | Bosselmann et al. |
| 5,960,129 | A | 9/1999 | Kleinschmitt |
| 5,993,194 | A | 11/1999 | Lemelson et al. |
| 6,016,372 | A | 1/2000 | Fein et al. |
| 6,018,413 | A | 1/2000 | Oka |
| 6,042,365 | A | 3/2000 | Chen |
| 6,064,417 | A | 5/2000 | Harrigan et al. |
| 6,124,597 | A | 9/2000 | Shehada et al. |
| 6,148,131 | A | 11/2000 | Geertman |
| 6,150,661 | A | 11/2000 | Mccaul et al. |
| 6,160,255 | A | 12/2000 | Sausa |
| 2,163,713 | A | 1/2001 | Fritz |
| 6,169,830 | B1 | 1/2001 | Kewitsch et al. |
| 6,294,389 | B1 * | 9/2001 | Vitale, Jr. ............ G01M 15/108 436/56 |
| 6,297,504 | B1 | 10/2001 | Andreou |
| 6,345,134 | B1 | 2/2002 | Laming et al. |
| 6,351,587 | B1 | 2/2002 | Holland |
| 6,363,190 | B1 | 3/2002 | Chen |
| 6,366,355 | B1 | 4/2002 | Degroot |
| 6,385,372 | B1 | 5/2002 | Yang |
| 6,396,056 | B1 | 5/2002 | Lord |
| 6,434,302 | B1 | 8/2002 | Fidric et al. |
| 6,455,851 | B1 | 9/2002 | Lord et al. |
| 6,469,785 | B1 | 10/2002 | Duceneck et al. |
| 6,510,265 | B1 | 1/2003 | Giaretta et al. |
| 6,519,385 | B1 | 2/2003 | Green |
| 6,542,679 | B2 | 4/2003 | DiGiovanni et al. |
| 6,593,573 | B1 | 7/2003 | Mccann et al. |
| 6,678,451 | B2 | 1/2004 | Kim et al. |
| 6,701,753 | B2 | 3/2004 | Dong et al. |
| 6,766,070 | B2 | 7/2004 | Williams et al. |
| 6,791,689 | B1 | 9/2004 | Weckström |
| 6,903,822 | B2 | 6/2005 | Kakuho et al. |
| 7,075,629 | B2 | 7/2006 | Bonne |
| 7,075,653 | B1 | 7/2006 | Rutherford |
| 7,080,504 | B2 | 7/2006 | Pais |
| 7,158,552 | B2 | 1/2007 | Buchold et al. |
| 7,248,755 | B2 | 7/2007 | Sappey et al. |
| 7,469,092 | B2 | 12/2008 | Sappey et al. |
| 8,448,495 | B2 * | 5/2013 | Breviere .................. G01N 1/40 250/343 |
| 8,544,279 | B2 | 10/2013 | Sappey |
| 8,711,353 | B2 * | 4/2014 | Kaye .................... G01J 3/02 250/575 |
| 8,786,856 | B2 | 7/2014 | Estes |
| 8,786,857 | B2 | 7/2014 | Masterson |
| 2001/0035952 | A1 | 11/2001 | Merklein |
| 2002/0031737 | A1 | 3/2002 | Von Drasek et al. |
| 2002/0158202 | A1 | 10/2002 | Webber et al. |
| 2002/0181856 | A1 | 12/2002 | Sappey et al. |
| 2003/0026541 | A1 | 2/2003 | Sappey et al. |
| 2003/0067952 | A1 | 4/2003 | Tsukiji et al. |
| 2003/0101774 | A1 | 6/2003 | Oh et al. |
| 2003/0174325 | A1 | 9/2003 | Zhang |
| 2003/0191397 | A1 | 10/2003 | Webb |
| 2004/0008744 | A1 | 1/2004 | Okazaki et al. |
| 2004/0019283 | A1 | 1/2004 | Lambert et al. |
| 2004/0065439 | A1 | 4/2004 | Tubel |
| 2004/0101305 | A1 | 5/2004 | Jung et al. |
| 2004/0160596 | A1 | 8/2004 | He et al. |
| 2005/0162655 | A1 | 7/2005 | Nadler |
| 2005/0191755 | A1 | 9/2005 | Balbach |
| 2006/0032471 | A1 | 2/2006 | Yalin |
| 2006/0087655 | A1 | 4/2006 | Augustine et al. |
| 2006/0147166 | A1 | 7/2006 | Roba et al. |
| 2006/0157239 | A1 | 7/2006 | Ramos |
| 2006/0176486 | A1 | 8/2006 | Ho |
| 2006/0243931 | A1 | 11/2006 | Haran |
| 2006/0278240 | A1 | 12/2006 | Spillman et al. |
| 2007/0133921 | A1 | 6/2007 | Haffner |
| 2007/0148478 | A1 | 6/2007 | Schmitz |
| 2007/0217744 | A1 | 9/2007 | Debut et al. |
| 2007/0285661 | A1 * | 12/2007 | Saunders ............ G01N 15/1459 356/336 |
| 2007/0296966 | A1 | 12/2007 | Benicewicz et al. |
| 2008/0002186 | A1 | 1/2008 | Masterson et al. |
| 2008/0013887 | A1 | 1/2008 | Sappey |
| 2008/0074645 | A1 | 3/2008 | Sappey |
| 2008/0262359 | A1 | 10/2008 | Tearney et al. |
| 2008/0289342 | A1 | 11/2008 | Sappey |
| 2009/0002684 | A1 | 1/2009 | Sanders |

(56) References Cited

U.S. PATENT DOCUMENTS

| | | | |
|---|---|---|---|
| 2009/0080054 | A1 | 3/2009 | Koyata et al. |
| 2009/0207413 | A1 | 8/2009 | Carpenter |
| 2009/0252451 | A1 | 10/2009 | Lagakos |
| 2010/0068871 | A1 | 3/2010 | Tian et al. |
| 2010/0171956 | A1 | 7/2010 | Sappey |
| 2011/0045420 | A1 | 2/2011 | Tanca |
| 2011/0188039 | A1 | 8/2011 | Aoyama |
| 2011/0300492 | A1* | 12/2011 | Estes .................. F23M 5/08 431/2 |
| 2012/0025112 | A1 | 2/2012 | Li |

FOREIGN PATENT DOCUMENTS

| | | |
|---|---|---|
| CN | 1938621 A | 3/2007 |
| DE | 2730508 A1 | 1/1979 |
| EP | 0766080 A1 | 4/1997 |
| EP | 1003595 | 9/2000 |
| EP | 1052868 A2 | 11/2000 |
| EP | 1205736 A | 5/2002 |
| GB | 2127174 A | 4/1984 |
| JP | S58 213235 | 12/1983 |
| JP | 63-133035 | 6/1988 |
| JP | 4-251214 | 9/1992 |
| JP | 07-504828 | 6/1995 |
| JP | H09-073020 | 3/1997 |
| JP | 09-152126 | 6/1997 |
| JP | 1998-2750609 | 10/1998 |
| JP | 10-301153 | 11/1998 |
| JP | 2000-074830 | 3/2000 |
| JP | 2000-121558 | 4/2000 |
| JP | 2001-215343 | 8/2001 |
| JP | 2002-236227 | 8/2002 |
| JP | 2003-084324 | 3/2003 |
| JP | 2003-156698 A | 5/2003 |
| JP | 2003-322568 | 11/2003 |
| JP | 2004-117236 | 4/2004 |
| JP | 2004-204787 A | 7/2004 |
| JP | 2004-354671 A | 12/2004 |
| JP | 2006-522938 | 10/2006 |
| JP | 2007-534983 | 11/2007 |
| JP | 2009-515079 | 4/2009 |
| KR | 10-2006-0008314 | 1/2006 |
| RU | 2163713 C2 | 4/2000 |
| RU | 77441 U1 | 10/2008 |
| RU | 2336573 C1 | 10/2008 |
| WO | WO 92/09877 | 6/1992 |
| WO | WO 00/28304 | 5/2000 |
| WO | WO 2004/051211 | 6/2004 |
| WO | WO 2004/090496 A2 | 10/2004 |
| WO | WO 2005/103781 A1 | 11/2005 |
| WO | WO 2007/087081 | 8/2007 |
| WO | WO 2008/065336 | 6/2008 |
| WO | WO 2008/103837 A1 | 8/2008 |
| WO | WO 2008/147994 | 12/2008 |
| WO | WO 2009/052157 | 4/2009 |
| WO | WO 2009/060572 | 4/2009 |
| WO | WO 2009/061586 | 5/2009 |
| WO | WO 2010/080892 | 7/2010 |
| WO | WO 2010/129073 | 11/2010 |
| WO | WO 2011/019755 A1 | 2/2011 |

OTHER PUBLICATIONS

Allen et al. (2002) "Tunable Diode Laser Sensing and Combustion Control" Applied Combustion Diagnostics, chapter 18.
Baer et al. (1994) "Multiplexed Diode-Laser Sensor System for Simultaneous H20, 02, and Temperature Measurements" Optics Letters 19(22):1900-1902.
Docquier and Candel (2002) "Combustion control and sensors: a review" Progress in Energy and Combustion Science 28, 107-150.
Ebert et al. (1998) "Simultaneous Laser-Based in situ Detection of Oxygen and Water in a Waste Incinerator for Active Combustion Control Purposes" 27th Symposium on Combustion pp. 1301-1308.
Ebert et al. (2000) "Simultaneous Diode-Laser-Based In Situ Detection of Multiple Species and Temperature in a Gas-Fired Power Plant" Proceedings of the Combustion Institute 28:423.
Ebert et al. (2000) "The Use of Lasers as the Basis for Combustion Equipment Control" at TOTem, Intelligent Combustion Control pp. 1-15.
English translation of a Japanese Office action received Apr. 8, 2010 for corresponding JP Application No. 2007-506152.
English translation of Chinese Office action received Mar. 25, 2010 for corresponding CN Application No. 200580010448.0.
European Patent Office Supplementary English Search Report from EP 10 80 8655 dated Dec. 19, 2014.
Furlong et al. (1998) "Diode Laser Sensors for Real-Time Control of Pulsed Combustion Systems": AIAA/SAE/ASME/ASEE Joint Propulsion Conference and Exhibit, pp. 1-8, 1, XP001148178.
Furlong et al. (1998) "Real-Time Adaptive Combustion Control Using Diode-Laser Absorption Sensors," 27th Symposium on Combustion pp. 103-111.
International Preliminary Report on Patentability, Written Opinion and International Search Report from PCT/US10/020345, dated Jul. 21, 2011 and Jun. 29, 2010.
International Search Report and Written Opinion from PCT/US05/02853, dated Aug. 29, 2005.
International Search Report and Written Opinion from PCT/US06/60572, dated Mar. 6, 2008.
International Search Report from PCT/US2008/079962, dated Feb. 27, 2009.
International Search Report and Written Opinion from PCT/US08/079935, dated Aug. 21, 2009.
International Search Report and Written Opinion from PCT/US10/020132, dated Oct. 8, 2010.
International Search Report and Written Opinion from PCT/US10/020345, dated Jun. 29, 2010.
International Search Report and Written Opinion from PCT/US10/045077, dated Oct. 4, 2010.
International Search Report and Written Opinion from PCT/US13/032479, dated Jun. 28, 2013.
Liu et al. (2003) "Diode Laser Absorption Diagnostics for Measurements in Practical Combustion Flow Fields" 39th AIAA/ASME/SAE/ASEE Joint Propulsion Conference and Exhibit, Paper No. AIAA-2003-4581 pp. 1-6.
Masiyano et al. (2008) "Use of Diffuse Replections in Tunable Diode Laser Absorption Spectroscopy Implications of Laser Speckle for Gas Absorption Measurements" Applied Physics B 90:279-288.
Miller et al. (1996) "Diode laser-based air mass flux sensor for subsonic aeropropulsion inlets" Applied Optics 35:4905.
Office Action dated Apr. 6, 2009 from the corresponding European application No. 06850383.8.
Ouyang et al. (1992) "Tomographic Absorption Spectroscopy of Combustion Gases using Tunable Infrared Diode Lasers," Paper No. 1637-20, SPIE Conference on Environmental and Process Monitoring Technologies, pp. 163-172.
Phillippe et al. (1993) "Laser diode wavelength-modulation spectroscopy for simultaneous measurement of temperature, pressure, and velocity in shock-heated oxygen flows" Applied Optics 32:6090.
Sanders et al. (2000) "Diode-Laser Sensor for Monitoring Multiple Combustion Parameters in Pulse Detonation Engines" Proceedings of the Combustion Institute 28:587.
Sanders et al. (2001) "Diode-laser absorption sensor for line-of-sight gas temperature distributions" Applied Optics 40:4404.
Severin et al. (1988) "A Simple Mulitmode Fibre Interferometric Sensor for Pressure-Related Measurements"Philips J. Res. 43:137-151.
Severin et al. (1989) "Bandwith and Modal Noise Effects in Fused-Head-End Multimode Fiber Passive Components" Journal of Lightwave Technology, vol. 7, No. 12, pp. 11-19.
Settles, et al (1995) Flow Visualization VII, ed. J.P. Crowder, Begell House, NY, Sep. 1995, pp. 2-13.
Supplemental European Search Report for Application No. EP 06850383, mailed on Mar. 5, 2009.
Supplemental European Search Report for Application No. EP 10729501.6, mailed on Nov. 27, 2013.

(56) References Cited

OTHER PUBLICATIONS

Teichert et al. (2003) "Simultaneous in situ measurement of CO H2O, and gas temperatures in a full-sized coal-fired power plant by near-infrared diode lasers" Applied Optics 42:2043.

Upschulte et al. (1999) "Measurements of CO, CO2, OH, and H2O in room-temperature and combustion gases by use of a broadly current-tuned multisection InGaAsP diode laser" Applied Optics 38:1506.

Varghese et al. (1997) "Temperature and CO2 Concentration Profiles in Flames Measured by Laster Absorption Tomography," Paper 97-0317, AIAA 35th Aerospace Sciences Meeting, Reno, NV.

Villarreal and Varghese (2005) Applied Optics 44:6786-6795, Frequency-resolved absorption tomography with tunable diode lasers.

Webber et al. (2000) "In Situ Combustion Measurements of CO, CO2, H2O and Temperature Using Diode Laser Absorption Sensors" Proceedings of the Combustion Institute 28:407.

Wolfrum (1998) "Lasers in Combustion: From Basic Theory to Practical Devices" 27th Symposium on Combustion pp. 1-41.

European Patent Office English Search Report from EP 13779007 dated Nov. 30, 2015.

* cited by examiner

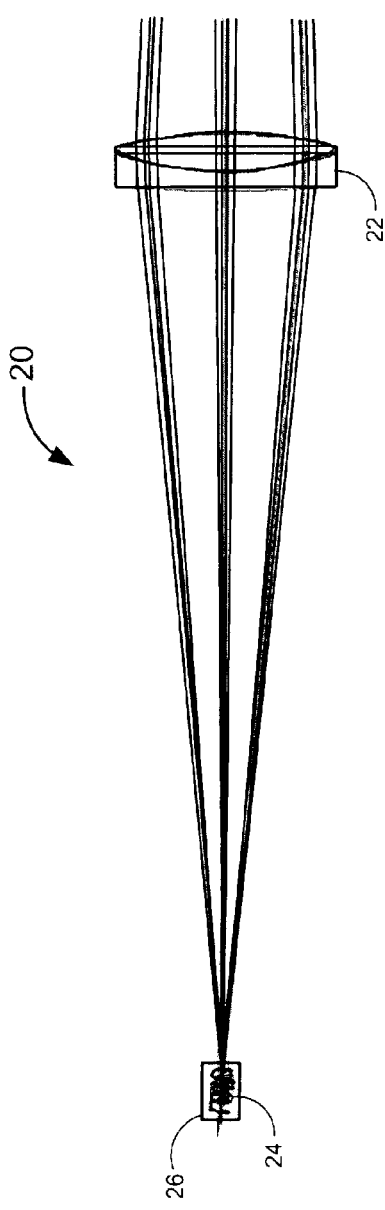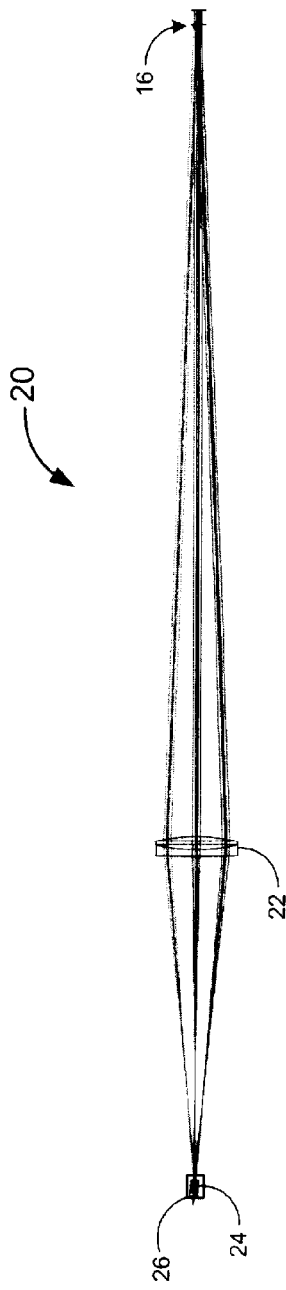
FIG. 2A
FIG. 2B

IN-FURNACE RETRO-REFLECTORS WITH STEERABLE TUNABLE DIODE LASER ABSORPTION SPECTROMETER

RELATED APPLICATIONS

This application is a 35 U.S.C. §371 national phase application of PCT/US2013/032479 (WO 2013/158311), filed on Mar. 15, 2013, entitled "In-Furnace Retro-Reflectors with Steerable Tunable Diode Laser Absorption Spectrometer", which application claims the benefit of U.S. Provisional Application Ser. No. 61/635,733, filed Apr. 19, 2012, which is incorporated herein by reference in its entirety.

TECHNICAL FIELD

The present disclosure is directed toward a method and apparatus for measuring combustion properties in an interior of a boiler or furnace, and more particularly toward a method and apparatus for measuring combustion properties in a boiler or furnace utilizing in-furnace retro-reflectors in conjunction with a steerable tunable diode laser absorption spectrometer.

BACKGROUND

U.S. Pat. No. 7,469,092, describes a method and apparatus for the monitoring and control of a process using tunable diode laser absorption spectroscopy (TDLAS). Briefly stated, the TDLAS method and apparatus involves directing a beam of light, which may be a multiplexed beam of a number of distinct wavelengths, into a boiler or furnace combustion chamber to measure boiler or furnace combustion properties such as temperature and the concentration of various combustion species including CO, $CO_2$, $O_2$ and $H_2O$. TDLAS monitoring techniques are based on a predetermined relationship between the quantity and nature of laser light received by a detector after the light has been transmitted through a region of interest and absorbed in specific spectral bands which are characteristic of the gas species resulting from combustion. The absorption spectrum received by the detector may be used to determine the quantity of a gas species under analysis plus associated combustion parameters such as temperature.

The technique requires a line of sight through the boiler or furnace. In fact, many lines of sight are typically required as it is often desirable to measure combustion properties in multiple boiler or furnace locations. Typically a wavelength multiplexed laser beam is transmitted from a pitch optic to a catch optic on the opposite side of the boiler or furnace. Certain applications require up to 15 or more measurement paths, thus requiring 15 or more pitch/catch optic pairs and 30 or more furnace penetrations. However, the use of 15 or more pairs of substantially identical pitch/catch optics and the need for 30 or more corresponding furnace penetrations imposes high costs, not to mention increasing the complexities of the system. In some cases, installation of the system may require waiting years for the scheduled shut-down of the boiler or furnace.

Because of the costs and complexities of the optics and corresponding furnace penetrations, the practicality of the conventional system is limited in the case where one desires to monitor (and perhaps also control) a larger number of combustion zones within the furnace.

The present invention is directed toward overcoming one or more of the problems discussed above.

SUMMARY OF THE EMBODIMENTS

A first aspect of the disclosure is a method of monitoring combustion properties in an interior of a combustion furnace (including, but not limited to, temperatures and concentrations of various combustion species). The method comprises providing at least one penetration in a wall of the furnace; providing at least two retro-reflecting surfaces within an interior of the furnace; projecting a beam of light through an optic comprising a collimating lens residing outside the interior of the furnace, the collimating lens being optically coupled to the at least one penetration to project the beam into the interior of the furnace toward a first retro-reflecting surfaces of the at least two retro-reflecting surfaces; receiving the beam of light from the first retro-reflecting surfaces with the optic; measuring the combustion properties based on the received beam of light from the first retro-reflecting surfaces; steering the beam of light through the optic to a second retro-reflecting surface of the at least two retro-reflecting surfaces; receiving the beam of light from the second retro-reflecting surface with the optic; and measuring the combustion properties based on at least the received beam of light from the second retro-reflecting surface. As used herein, a retro-reflector is broadly defined as an optical device that redirects incident laser light back towards its source, regardless of the angle of incidence, so long as the beam is incident on an aperture of the retro-reflector.

According to some embodiments, the beam of light is propagated/projected through a multimode fiber and through the optic comprising the collimating lens, reflected from one of the retro-reflecting surfaces, received by the same collimating lens, and propagated in the reverse direction within the same multimode fiber.

In some embodiments, the at least one penetration includes one of circular penetrations and penetrations elongated parallel to a plurality of parallel steam tubes separated by metal membranes incorporated in the wall of the furnace. For example, some boilers of coal fired electrical generation plants require parallel steam tubes. For furnaces without the steam tubes, any shape of penetrations (e.g., triangle, square, rectangle, ellipse, other polygons, etc.) may be utilized, so long as the beam can be effectively projected and/or received therethrough.

According to some embodiments, each of the at least two retro-reflecting surfaces is made of a material selected from the group consisting of sapphire and quartz. In one embodiment, each of the at least two retro-reflecting surfaces is one of a single, large retro-reflector or an array of smaller retro-reflector elements. In some embodiments, the at least two retro-reflecting surfaces includes at least one of a corner cube retro-reflecting optic or a cat's eye retro-reflecting sphere. In some embodiments, the first and second retro-reflecting surfaces are first and second portions of a single retro-reflecting surface comprising an array of discrete retro-reflectors, and wherein steering from the first retro-reflecting surface to the second retro-reflecting surface is steering from the first portion to the second portion of the single retro-reflecting surface.

As used herein, reference to, or mention of, retro-reflector(s) may mean any of (a) a single, large retro-reflector located at a discrete position in a furnace for which one may desire to monitor and/or control combustion processes (e.g., a "discrete retro-reflector"), (b) an array of smaller discrete retro-reflector elements (i.e., a "retro-reflector array" or "array retro-reflector") that take the place of the single, large retro-reflector described in (a).

According to some embodiments, the method further includes providing a mounting structure for mounting each retro-reflecting surface within the interior of the furnace positioned on a side of the furnace opposite to a side of the interior of the furnace on which flame-emitting burners are located, wherein each of the at least two retro-reflectors is configured to be secured to a mounting structure. The at least one mounting structure may include a ceramic mounting structure having slots in which each retro-reflector is held. Alternatively, nichrome wire (which may be made of, e.g., nichrome alloy including 80% nickel and 20% chromium) may be used to secure each of the retro-reflectors to a mounting structure. In some embodiments, the furnace includes a ceiling and a floor, the ceiling and floor are substantially perpendicular to the wall of the furnace, and wherein the flame-emitting burners are mounted to the ceiling, while each mounting structure is mounted to the floor. Embodiments could also include more than one retro-reflector attached to a mounting structure. For example, in embodiments where the retro-reflector comprises a plurality of small retro-reflectors, and even in embodiments where two or more larger retro-reflectors are attached to a single mounting structure.

Based on some embodiments, providing the at least two retro-reflectors within the interior of the furnace includes arranging a plurality of retro-reflectors in at least one of a single-plane configuration, a multi-plane configuration, a pre-arranged configuration, and an arbitrary configuration throughout the interior of the furnace. In some embodiments, each plane of the single-plane configuration and the multi-plane configuration is either perpendicular to the wall of the furnace or parallel to the beam of light projected through the optic.

According to some embodiments, steering the beam using the optic includes tilting the optic about at least one of two orthogonal axes that are perpendicular to an optical axis of the at least one penetration.

According to one embodiment, receiving the beam of light includes receiving the beam in a multimode optical fiber, and wherein measuring the combustion properties includes filtering noise by averaging modal noise induced signal level variation of light propagating within the multimode optical fiber.

According to some embodiments, providing the at least two retro-reflectors includes providing a plurality of retro-reflectors positioned within the interior of the furnace to monitor combustion zones within the furnace, wherein projecting the beam of light includes projecting the beam toward each of the plurality of retro-reflectors, and wherein measuring the combustion properties includes calculating the combustion properties by taking into account measurements of the beam reflected and received from each zone.

In some embodiments, the optic further includes a relay lens residing outside the interior of the furnace, the relay lens being optically coupled to the collimating lens and optically coupled to the at least one penetration to project the beam into the interior of the furnace toward each of the first and second retro-reflectors of the at least two retro-reflectors.

A second aspect of the disclosure is an apparatus for sensing combustion properties in an interior of a combustion furnace (including, but not limited to, temperatures and concentrations of various combustion species). The apparatus comprises a diode laser, a collimating lens, at least two retro-reflectors; a kinematic tilt stage, and a detector. The diode laser has a select lasing frequency. The collimating lens is optically coupled to a beam generated by the diode laser, the collimating lens being configured to project the beam from the diode laser into a penetration in a wall of the furnace. The at least two retro-reflectors are positioned within an interior of the furnace, and each are configured to reflect the beam from the collimating lens back to the collimating lens. The kinematic tilt stage includes at least one stepper motor, a motor drive, and a stage coupled to the t collimating lens. The at least one stepper motor is configured to tilt the stage about at least one of two orthogonal axes that are perpendicular to an optical axis of the first penetration, so as to steer the beam of light from one to another of the at least two retro-reflectors. The detector is of a type that is sensitive to the select lasing frequency optically coupled to the collimating lens.

The apparatus, according to some embodiments, further comprises a multimode fiber through which the beam is propagated from the diode laser to the collimating lens. The collimating lens is configured to project the beam from the diode laser and the multimode fiber through a penetration to one of at least two retro-reflecting surfaces positioned in the interior of the furnace. The collimating lens is further configured to receive the reflected beam from said one of at least two retro-reflecting surfaces, and to transmit the reflected beam back through the same multimode fiber, to the detector, which is optically coupled to the multimode fiber.

According to some embodiments, the first penetration includes one of circular penetrations and penetrations elongated parallel to a plurality of parallel steam tubes separated by metal membranes incorporated in the wall of the furnace. Typically only boilers require the parallel steam tubes. For furnaces without the steam tubes, any shape of penetrations may be utilized, so long as the beam can be effectively projected and/or received therethrough.

In some embodiments, each of the at least two retro-reflectors is made of a material selected from the group consisting of sapphire and quartz. In one embodiment, each of the at least two retro-reflectors is an array of smaller retro-reflector elements. In some embodiments, the at least two retro-reflectors includes at least one of a corner cube retro-reflecting optic and a cat's eye retro-reflecting sphere.

According to some embodiments, the apparatus further comprises a mounting structure for mounting each retro-reflecting surface within the interior of the furnace positioned on a side of the furnace opposite to a side of the interior of the furnace on which flame-emitting burners are located, wherein each of the at least two retro-reflectors is configured to be secured to a mounting structure. In one embodiment, each mounting structure includes a ceramic mounting structure having slots in which each retro-reflector is held. In another embodiment, each of the at least two retro-reflectors is secured via a one mounting structure via nichrome wire (which may be made of, e.g., nichrome alloy including 80% nickel and 20% chromium). Embodiments could also include more than one retro-reflector attached to a mounting structure. For example, in embodiments where the retro-reflector comprises a plurality of small retro-reflectors, and even in embodiments where two or more larger retro-reflectors are attached to a single mounting structure.

Based on some embodiments, the furnace includes a ceiling and a floor, the ceiling and floor are substantially perpendicular to the wall of the furnace, and wherein the flame-emitting burners are mounted to the ceiling, while each mounting structure is mounted to the floor.

In several embodiments, the at least two retro-reflectors includes a plurality of retro-reflectors arranged in at least one of a single-plane configuration, a multi-plane configuration, a pre-arranged configuration, and an arbitrary configuration throughout the interior of the furnace. In some embodiments, each plane of the single-plane configuration and the multi-plane configuration is either perpendicular to the wall of the furnace or parallel to the beam of light projected through the optic.

In some embodiments, the at least two retro-reflectors includes a plurality of retro-reflectors positioned within the interior of the furnace for monitoring combustion zones within the furnace, wherein the collimating lens projects the beam toward each of the plurality of retro-reflectors, and wherein the detector calculates the combustion properties by taking into account measurements of the beams reflected and received from each zone.

The apparatus, according to some embodiments, further includes a relay lens. The relay lens is optically coupled to the collimating lens and the penetration, and is configured to project the beam from the diode laser, through the collimating lens and the penetration, to the at least two retro-reflectors.

A third aspect of the disclosure is directed to a computer software stored on a recordable medium that when executed by a processor (e.g., one in a general purpose or application specific computer) causes the processor to: access a database to determine locations of retro-reflectors within an interior of a furnace; send instructions to a motor drive for driving at least one stepper motor for tilting a stage on which transmit/receive optics are housed, so as to steer a beam projected from the transmit/receive optics to one of the retro-reflectors based on the determined location of the retro-reflectors; receive and store a signal from a detector optically coupled to the transmit/receive optics that has detected the beam reflected back to the transmit/receive optic from said one of the retro-reflectors; and calculate combustion properties based on the received and stored signal from the detector.

In some embodiments, the computer software when executed by the processor further causes the processor to: send instructions to the motor drive, so as to jump the beam to each of the retro-reflectors within a first predetermined zone of the furnace, based on the determined location of the retro-reflectors; receive and store signals from the detector that has detected the beam reflected back to the transmit/receive optic from said each of the retro-reflectors within the first predetermined zone of the furnace; and calculate combustion properties of the first predetermined zone based on the received and stored signals from the detector.

According to some embodiments, the computer software when executed by the processor further causes the processor to: send instructions to the motor drive, so as to jump the beam to each of the retro-reflectors within a second predetermined zone of the furnace, based on the determined location of the retro-reflectors; receive and store signals from the detector that has detected the beam reflected back to the transmit/receive optic from said each of the retro-reflectors within the second predetermined zone of the furnace; and calculate combustion properties of the second predetermined zone based on the received and stored signals from the detector, taking into account the calculated combustion properties of the first predetermined zone.

In some embodiments, the computer software when executed by the processor further causes the processor to: send instructions to the motor drive, so as to steer the beam to a plurality of portions of said one of the retro-reflectors; receive and store a calibration signal from the detector that has detected the beam reflected back from said plurality of portions of said one of the retro-reflectors; determine an optimal position based on which of the plurality of portions of said one of the retro-reflectors reflects the strongest calibration signal; and send instructions to the motor drive, so as to steer the beam to the optimal position. This auto-alignment feature allows the transmit/receive optics to maintain optical alignment with the in-furnace retro-reflector and with itself, even though the transmit/receive optics and the retro-reflector are bolted onto a furnace or hostile process chamber which is, itself, subject to movement from thermal effects or wind and vibration.

The method and apparatus for measuring combustion properties in an interior of a furnace described herein allows for detection of combustion properties without having to use separate pitch and catch optics, which results in at least half the number of necessary ports and optical setup and alignment equipment. The method and apparatus additionally allows for further reducing the number of optical setup and alignment equipment by utilizing steerable tunable diode laser absorption spectroscopy systems in conjunction with an array of in-furnace retro-reflectors, which together allow for a maximum number of beam paths with a minimum number of optical setup and alignment equipment. The method and apparatus therefore allow the many benefits of combustion monitoring to be enjoyed efficiently, inexpensively, and with less complexity, as compared to systems that do not utilize either a combination pitch/catch optic and/or steerable tunable diode laser absorption spectroscopy systems coupled to in-furnace retro-reflectors.

BRIEF DESCRIPTION OF THE DRAWINGS

FIGS. 2A and 2B illustrate steerable pitch/catch optics for steering the beam within the interior of the boiler or furnace.

DETAILED DESCRIPTION

Figure 1B:
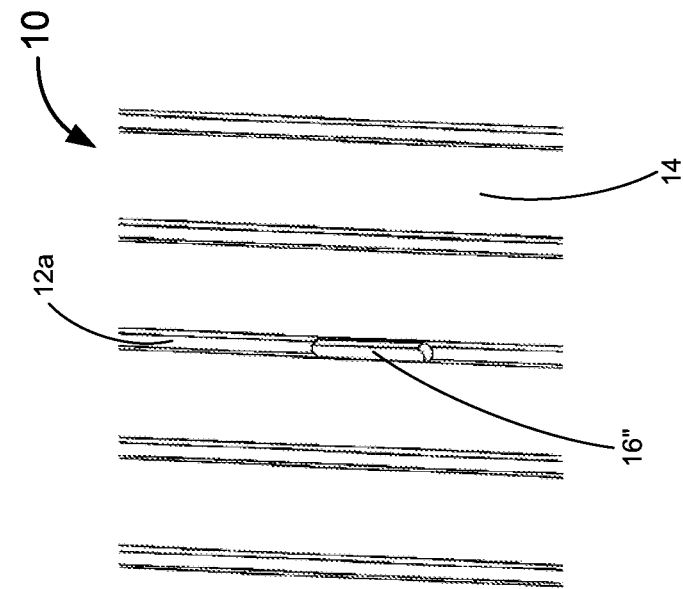
FIGS. 1A and 1B illustrate alternative penetrations in the wall of a boiler or furnace for providing optical access to the boiler or furnace interior.

Unless otherwise indicated, all numbers expressing quantities of ingredients, dimensions, reaction conditions, and so forth used in the specification and claims are to be understood as being modified in all instances by the term "about."

In this application and the claims, the use of the singular includes the plural unless specifically stated otherwise. In addition, use of "or" means "and/or" unless stated otherwise. Moreover, the use of the term "including," as well as other forms, such as "includes" and "included," is not limiting. Also, terms such as "element" or "component" encompass both elements and components comprising one unit and elements and components that comprise more than one unit unless specifically stated otherwise.

U.S. Pat. No. 7,469,092, the contents of which are hereby incorporated herein in their entirety, discloses a method and apparatus for monitoring and control of a combustion process of the type requiring installation of tube bends in the wall of a boiler in order to provide optical access to the boiler. U.S. Pat. No. 7,469,092 describes a sensing system which incorporates an auto-alignment feature that allows the pitch and catch optics to maintain optical alignment even though they are bolted onto a boiler or hostile process chamber which is, itself, subject to movement from thermal effects or wind and vibration. The described system provides separate pitch and catch optics including separate pitch and catch collimating lenses that are mounted on feedback-control tilt stages. Multiplexed light is launched across the measurement region by a collimating pitch lens attached directly to an input fiber and the catch collimating lens, located at the opposite end of the measurement region, optically couples transmitted light to an output fiber that is typically a multi-mode fiber. As a result, the catch optic must be oriented so that it is collinear with the beam emanating from the pitch optic. This is necessary so that the focused transmitted beam will arrive within the acceptance cone of the multi-mode fiber.

Hereinafter, the terms "boiler" and "furnace" will be used interchangeably to refer to any combustion chamber for which monitoring and control of the combustion process is desired.

With reference to FIGS. 1-10 and in contrast to the system described in U.S. Pat. No. 7,469,092, the system according to various embodiments provides a combination pitch/catch optic including pitch/catch collimating lens that is mounted on feedback-control tilt stages. Multiplexed light is launched across the measurement region by a collimating pitch lens attached directly to an input fiber and the collimating catch lens optically couples transmitted light to an output fiber that is typically a multi-mode fiber. Here, the collimating pitch lens and the collimating catch lens are embodied in the same collimating lens. The multiplexed light that is launched across the measurement region is reflected back to the source by at least one retro-reflector that is positioned in the furnace. A retro-reflector is an optical device that redirects incident laser light back towards its source regardless of the angle of incidence, provided the beam hits an entrance to an aperture of the retro-reflector.

Figure 1A:
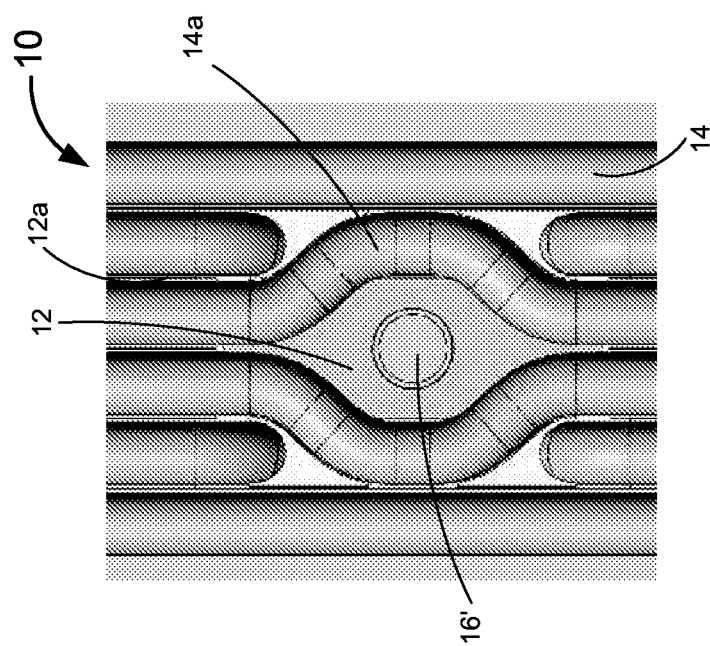

FIGS. 1A and 1B illustrate two examples of penetrations 16 in the wall 12 of the furnace 10 for providing optical access to the furnace interior. FIG. 1A illustrates a boiler wall 12 comprising a series of parallel steam tubes 14 separated by a metal membrane 12a. Tube bends 14a, as illustrated in FIG. 1A, are provided to reroute steam tubes 14 around a penetration, which may be for example a 2" (5.08 cm) diameter circular penetration 16'.

FIG. 1B illustrates an alternative embodiment, which is described in WO 2010/080892 A2, the contents of which are hereby incorporated herein in their entirety. FIG. 1B illustrates a slotted membrane penetration 16" that has approximately a ½ inch (1.27 cm) width (equal to the width of the membrane 12a) and is elongate in a direction parallel to the steam pipes 14. This arrangement eliminates the need for providing tube bends 14a (as shown in FIG. 1A), while somewhat aiding in terms of light collection efficiency. Alignment and maintenance of alignment, however, are significantly more difficult than required with the 2 inch (5.08 cm) circular penetration 16' supported by the tube bend approach, as shown in FIG. 1A, and requires a tighter alignment tolerance.

Although the embodiments shown in FIGS. 1A and 1B are directed to a boiler having steam tubes in the walls of the boiler, the embodiments are not so limited, and may apply to any combustion chamber for which monitoring of combustion properties is desired. In such cases, the shape of the penetration 16 may be any shape (including, but not limited to, circular, substantially circular, elliptical, rectangular, triangular, square, other polygons, etc.), so long as it allows the beam to be effectively projected and received therethrough.

With reference to FIGS. 2A and 2B, various embodiments provide for a steering and alignment system 20 comprising relay lens 22, collimating lens 24, and adjustable stage 26. Relay lens 22 is provided in optical communication with collimating lens 24. Relay lens 22 is aligned during construction on the axis 30 (shown in, e.g., FIG. 3) of penetration 16 (including circular penetration 16', slotted membrane penetration 16", or other-shaped penetrations as described above). With the relay lens 22 aligned as such, the beam received by the relay lens 22 must go through the penetration 16 at what is the focal point of the relay lens 22. The angle that the beam goes through the penetration 16 can be adjusted in two dimensions by steering the beam from the collimating lens to different locations on the relay lens. This allows the beam to be steered through the penetration 16 to control the angle of incidence of the beam on a retro-reflector 42 (as shown in FIGS. 5-9) that is provided in the furnace, so as to reflect the beam back toward the relay lens 22 and collimating lens 24 of the steering and alignment system 20. Embodiments as illustrated in FIGS. 2A and 2B incorporating a relay lens would most often be favored in combustion chambers having narrow penetrations, such as illustrated in FIG. 1B.

Figure 3:
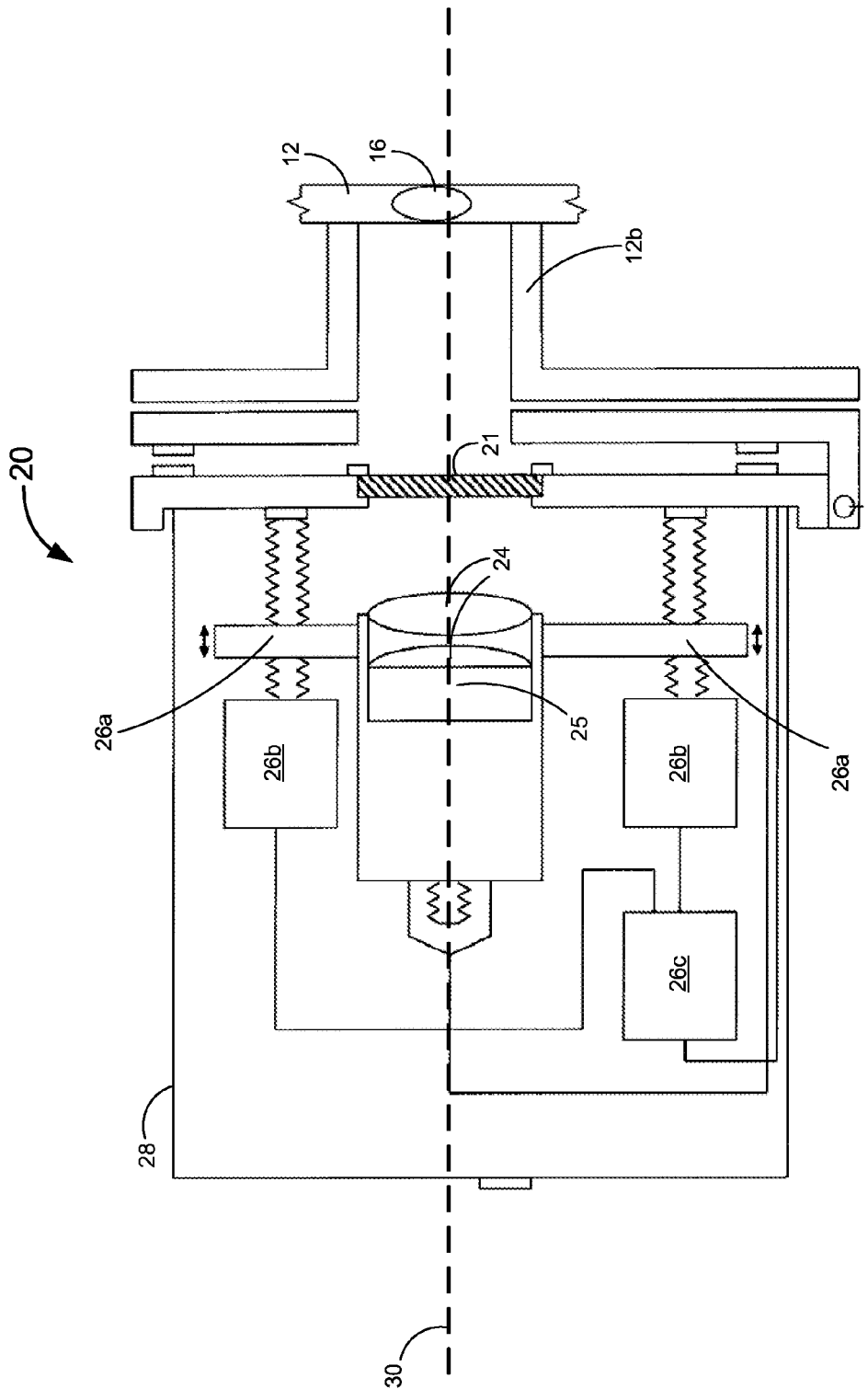
FIG. 3 is a schematic illustration of an embodiment of alignable and steerable pitch/catch optics.
Figure 4:
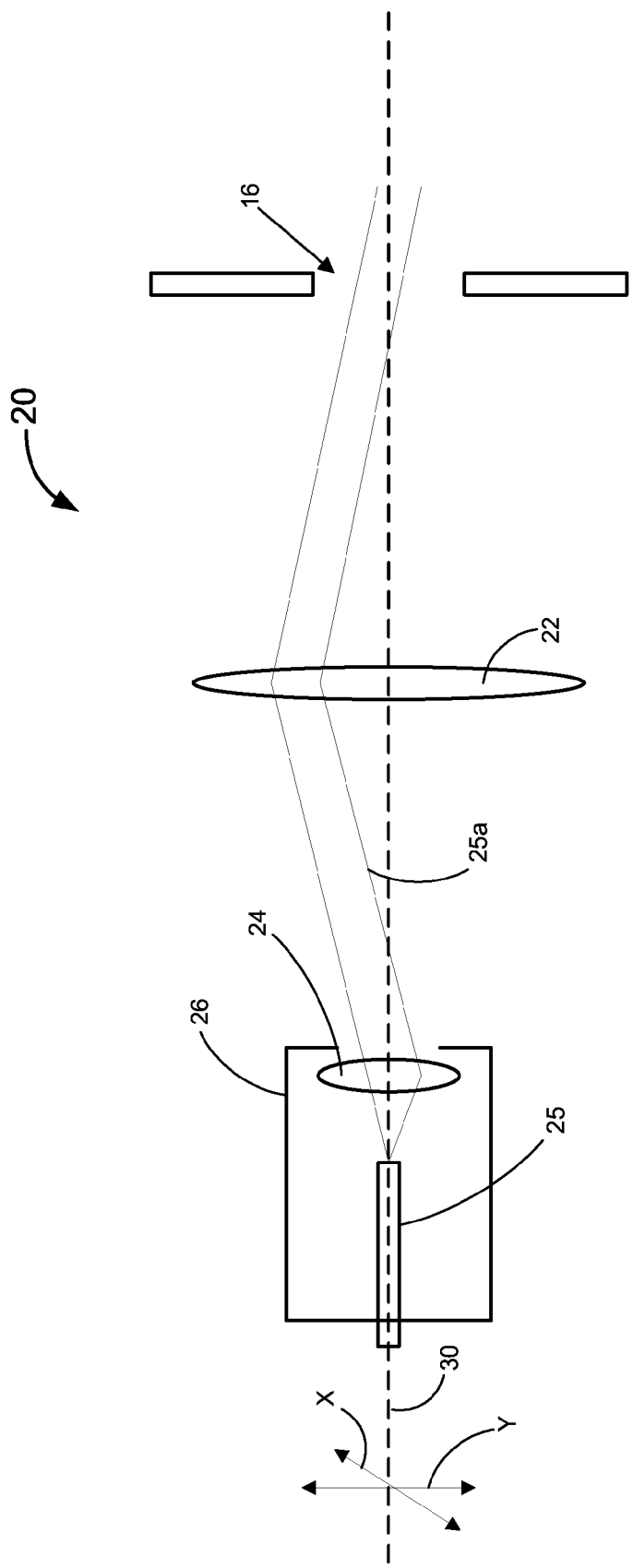
FIG. 4 is a schematic illustration of an alternative embodiment of alignable and steerable pitch/catch optics.
Figure 5:
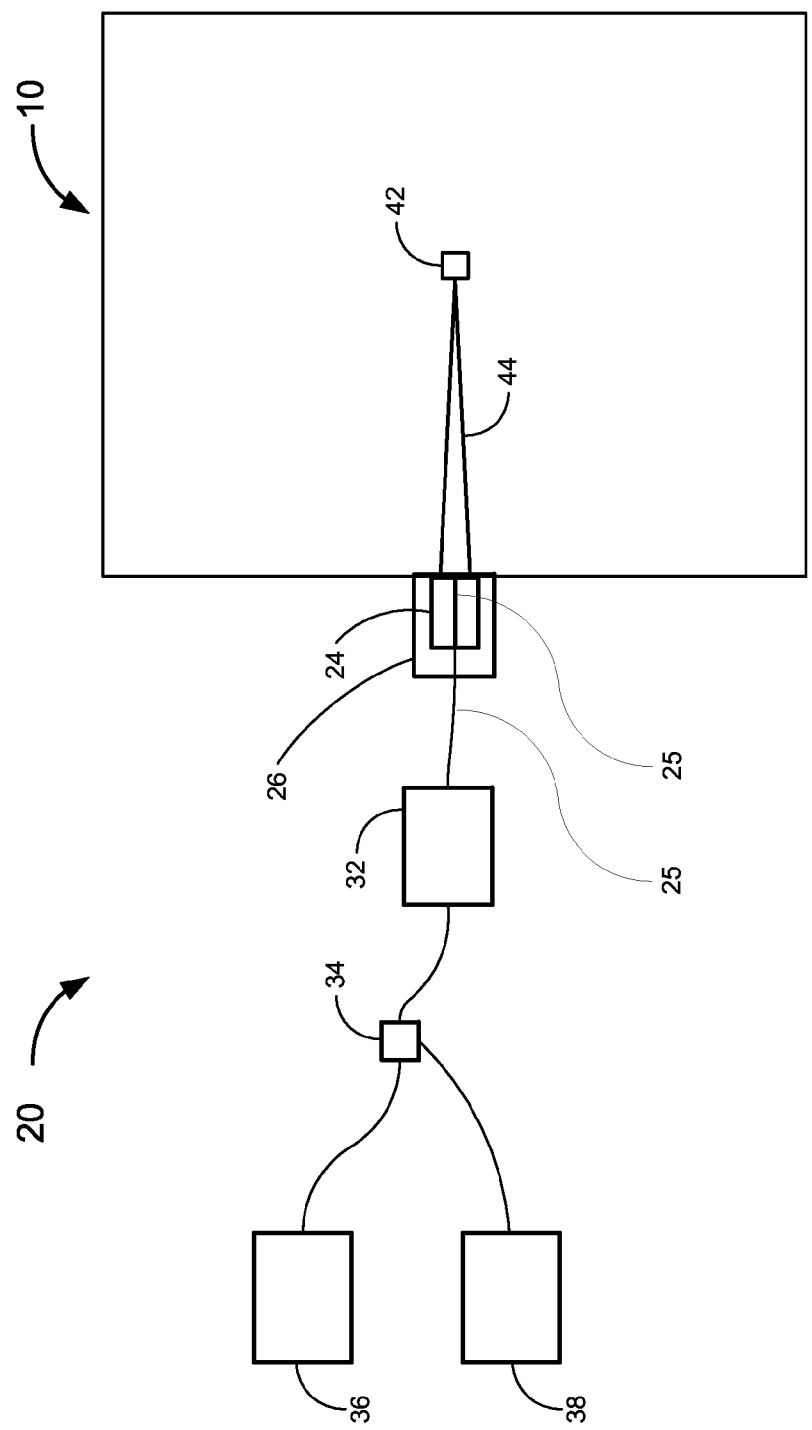
FIG. 5 is a schematic illustration of an embodiment of a steerable tunable diode laser absorption spectroscopy system with a combination pitch/catch optic used in conjunction with an array of in-furnace retro-reflectors.

As such, steering and alignment system 20 provides for an auto-alignment feature that allows the combination pitch and catch optics to maintain optical alignment with the in-furnace retro-reflector 42 and with itself, even though the steering and alignment system 20 and the retro-reflector 42 are bolted onto a boiler or hostile process chamber which is, itself, subject to movement from thermal effects or wind and vibration. Use of the adjustable stage 26 ensures a maximum strength collimated received beam is conveyed to an optically coupled multi-mode fiber 25 (as shown in FIGS. 3-5). To further provide effective optical coupling, the pitch beam is collimated to a diameter of about 5 mm, as opposed to on the order of 20 mm in prior art systems.

According to various embodiments, steering and alignment system 20 may be configured to steer the beam toward not only one retro-reflector 42, but each of a plurality of in-furnace retro-reflectors 42 (as shown, e.g., in FIGS. 7-9), which will be discussed in detail below.

FIG. 3 schematically illustrates an embodiment of steerable and alignable combination pitch/catch optics that serve as both the transmitter that generates a collimated beam of laser light emerging from an optical fiber 25 and the receiver that captures a collimated beam of light (reflected from one of a plurality of in-furnace retro-reflectors 42), and focuses the beam into the optical fiber 25.

The combination pitch/catch optics may be mounted in a housing 28 with the leading side having an orifice occupied by a window 21. The housing may be an NEMA-4 enclosure to protect the combination pitch/catch optics from the environment. As shown in FIG. 3, an embodiment includes collimating lens 24 attached to a kinematic tilt stage 26 positioned to tip and tilt the collimating lens 18 about orthogonal axes (i.e., X and Y axes) perpendicular to an optical axis 30 of the steerable and alignable combination pitch/catch optics. In various embodiments the collimating lens may be a singlet lens, a doublet lens or include more than two lenses. The kinematic tilt stage 26 includes stage 26a, two direct drive stepper motors 26b, and motor drive 26c. Stepper motors 26b are configured to tip and tilt the stage 26a about orthogonal axes X and Y that are perpendicular to optical axis 30, and are controlled by a computer via an Ethernet or similar connection. This connection may be through an optical fiber in order to avoid electrical interference. The stepper motors 26b hold their positions when power is removed, so optical alignment is not affected by power outages. The stepper motors 26b are driven by motor drive 26c.

During periodic or continuous system alignment, the control computer monitors the amount of laser light that is transmitted and detected. Preferably, a discrete alignment wavelength such as a visible or near-infrared light may be provided for continuous or periodic alignment proceedings. Any misalignment will reduce this detected signal. In auto-alignment mode, the computer measures the detected signal, directs one of the two stepper motors 26b to move a small amount in one direction, then re-measures the detected signal. If the signal increases, the computer directs one of the stepper motors 26b to move again in the same direction until the signal does not increase. The computer then directs the other stepper motor 26b to move along the orthogonal axis to maximize the detected signal, then repeats the whole process for the other sensor head. As the detected signal increases, the detector amplifier gain automatically decreases so that the auto-alignment proceeds over several iterations of signal size. The auto-alignment system can function with detected powers from nanowatts to milliwatts.

This "hill-climbing" algorithm is able to align the system after near-total loss of signal, in the presence of substantial noise, and is tolerant of beam blockages, power outages, mechanical shocks, and other disturbances that could cause other alignment systems to misalign to the limits of the control electronics. All that is required for auto alignment is a finite signal with a global maximum in position space. Depending on the specific installation conditions, auto-alignment may occur periodically at set intervals such as every hour or as needed after an extended period, such as days of operation. The control computer may monitor the directed signal and auto-align only when the signal drops below a preset threshold.

In some embodiments, the computer directs the beam to a second in-furnace retro-reflector 42 by directing the stepper motors 26b to "jump" to the second retro-reflector 42 by a predetermined or calculated angle. This can be done in a single plane in the case that the in-furnace retro-reflectors are arranged in an array in a single plane, such that "jumping" is performed in one dimension by driving stepper motors 26b about one orthogonal axis (e.g., X-axis) that is perpendicular to the optical axis of the steerable and alignable combination pitch/catch optics, so as to scan the beam along a single plane on which the array of in-furnace retro-reflectors lie. Alternatively, "jumping" may be performed in two dimensions by driving stepper motors 26b about the two orthogonal axes (e.g., X and Y axes) that are perpendicular to the optical axis of the steerable and alignable combination pitch/catch optics, in which case the in-furnace retro-reflectors 42 may be arranged so as to lie in multiple planes, in some prearranged pattern, or in arbitrary positions within the furnace. The one or more planes may be parallel to a floor of the furnace 10 or parallel with the beam, at a particular time that the beam is being emitted (in such a case, multiple planes would be displaced by predetermined or calculated angles with respect to each other).

Referring back to FIG. 3, in one embodiment a sight tube 12b has a proximal and a distal end. The proximal end is attached to extend normally from an exterior wall 12 of the furnace 10 with penetration 16 communicating with the interior of the sight tube 12b. A flange is provided at a distal end of the sight tube 12b. The flange allows the housing 28 to be attached with the leading end abutting the furnace flange with the window 21 in optical communication with the penetration 16. In this manner, a beam may be transmitted into the furnace interior through the penetration 16 and to reflect off at least one in-furnace retro-reflector 42 positioned in furnace 10 back to penetration 16 to pass through the window 21 and be captured by the collimating lens 24. In these embodiments, multimode optical fiber 25 would be configured to transmit the beam and receive the reflected beam.

FIG. 4 illustrates an alternative embodiment of steerable and alignable combination pitch/catch optics 20. In this alternative embodiment, a lens 24 is optically coupled to an optical fiber 25. The lens 24 is referred to herein as a "collimating" lens and may be a true collimating lens (that produces a beam of substantially constant diameter). Alternatively the collimating lens 24 may be a "near" collimating lens that provides a slight expansion of the beam 25a. The fiber 25 and the collimating lens 24 are mechanically linked together in a fixed relationship and movable by "translation" along orthogonal X-Y axes that are perpendicular to the optical axis 30 of the steerable and alignable combination pitch/catch optics, by a translation mechanism 26. The emitted beam 25a is movable by translation to strike select portions of the relay lens 22, which directs the beam through the membrane slot 16 and focuses the beam at about one of a plurality of in-furnace retro-reflectors 42 (as shown, e.g., in FIGS. 5-9). Stepper motors 26b (as shown, e.g., in FIG. 3), a computer controller 26c (as also shown, e.g., in FIG. 3), and a "hill climbing" algorithm similar to that discussed above with respect to the embodiment of FIG. 3 are operatively associated with the translation mechanism 26 to provide for substantially continuous alignment correction, and to provide for "jumping" between in-furnace retro-reflectors 42.

With reference to FIG. 5, various embodiments of steering and alignment system 20 is shown coupled to furnace 10 having at least one in-furnace retro-reflector 42 positioned therein. Steering and alignment system 20 includes a multimode optical fiber 25, transmit and receive optic 24, adjustable stage 26, noise reduction module 32, optical divider 34, tunable diode laser 36, and detector 38. In one embodiment, multimode optical fiber 25, transmit and receive optic 24, and adjustable stage 26 may be as described above with respect to any of the embodiments as shown, e.g., in FIGS. 2A to 4. The transmit and receive optic 24 may also include only a collimating lens without a relay lens 22. Noise reduction module 32 includes any type of noise reduction device. For example, noise reduction module 32 may include an averaging component, which may be operatively associated with the multimode optical fiber 25, in order to average modal noise induced signal level variation of light propagating within the multimode optical fiber 25. In one embodiment, the averaging component 32 is a mechanical vibrator. WO 2011/019755, the contents of which are hereby incorporated herein in their entirety, describes various systems and methods for reducing noise in a multimode optical fiber.

In some embodiments, the averaging component may average modal noise induced signal level variations by cyclically varying an index of refraction of the multimode optical fiber over a select period of time, scrambling a light distribution within the multimode optical fiber, or both. The index of refraction of the multimode optical fiber may be cyclically varied by cyclically varying the temperature of the multimode optical fiber. The index of refraction may be varied or the light distribution within the multimode optical fiber may be scrambled by cyclically and physically manipulating the multimode optical fiber.

In some embodiments, the temperature of the multimode optical fiber may be varied through the action of a thermal element placed in thermal communication with the multimode optical fiber. Suitable devices for use as a thermal element include, but are not limited to, a thermoelectric module, a resistive heater, an infrared heater, a chemical heater, a conventional refrigeration device, a chemical cooler, a source of fluid cooled below ambient temperature, or a source of fluid heated above ambient temperature. The optical device may include a temperature sensor such as a thermocouple in thermal contact with the multimode optical fiber and a controller receiving input from the temperature sensor and controlling the thermal element.

In an alternative embodiment, which features an apparatus for cyclically manipulating the multimode optical fiber, the manipulation may include twisting, stretching, or shaking the multimode optical fiber. A piezo stretcher may be used to accomplish the cyclical stretching of the multimode optical fiber. Alternatively, a motor may be used to cyclically twist a portion of the multimode optical fiber in alternate clockwise and counterclockwise directions with respect to the longitudinal axis of the fiber and relative to a fixed portion of the fiber. WO 2005/103781, the contents of which are hereby incorporated herein in their entirety, describes various apparatuses and methods for optical mode noise averaging, including the cyclically varying an index of refraction by one of cyclically varying the temperature of the multimode optical fiber and cyclically manipulating by twisting, stretching, or shaking the multimode optical fiber, as described above.

Referring again to FIG. 5, the multimode optical fiber 25 is optically coupled to the transmit and receive optic 24. The multimode optical fiber 25 is further optically coupled to a tunable diode laser 36, which produces a beam of light at a select wavelength. In one embodiment, an optical divider 34 is optically associated with the multimode optical fiber 25. The optical divider 34 may be, by way of example, a spatial multiplexer or a circulator of the type used in telecommunications applications. The function of the optical divider 34 is to divide optical signals received by the transmit and receive optic 24 from an optical signal generated by the tunable diode laser 36 and to deliver the received portion of the signal to a detector 38, which is typically a photo detector sensitive to the frequency of light generated by the tunable diode laser 36. In selected embodiments, the TDLAS sensor 20 is operatively associated with a portion of a combustion furnace 10 with a portion of the furnace 10 including an outer wall 12 and an internal space having at least one in-furnace retro-reflector 42 positioned therein.

A probe beam 44 generated by the tunable diode laser 36 is directed off the at least one in-furnace retro-reflector 42 so that it reflects back to the transmit and receive optic 24 as illustrated in FIG. 5. A portion of the transmitted beam received by the transmit and receive optic 24 is conveyed by the multimode optical fiber 25 to the optical divider 34 for detection by the detector 38. In some embodiments, noise reduction component 32 (which may include an averaging component, such as a mechanical vibrator) may be used to reduce modal noise induced signal variation of the light propagating within the multimode optical fiber 25 (e.g., by averaging the modal noise induced signal variations).

Figure 6:
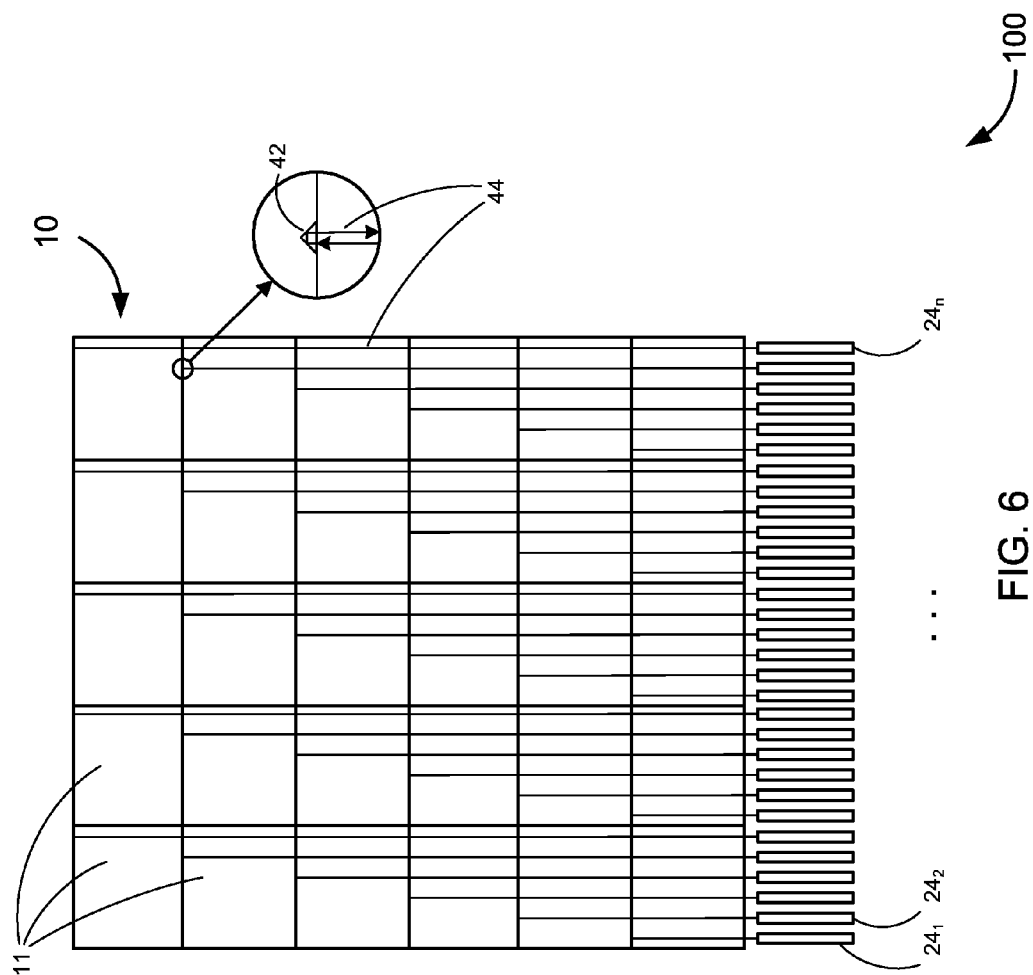
FIG. 6 is a top-view schematic illustration of an embodiment of an array of combination pitch/catch optics used in conjunction with an array of in-furnace retro-reflectors.

With reference to FIG. 6, an embodiment 100 is shown in which there is a one-to-one relationship between transmit and receive optics $24_{1\text{-}to\text{-}n}$ and the array of in-furnace retro-reflectors, such that the beam 44 from one transmit and receive optic $24_x$ is transmitted and reflected off only one of the plurality of in-furnace retro-reflectors 42 back toward said transmit and receive optic $24_x$. In this way, for 30 paths, 30 transmit and receive optics $24_{1\text{-}to\text{-}n}$ and 30 in-furnace retro-reflectors 42 would be required. Each of the plurality of retro-reflectors may be positioned in a grid 11 of the furnace 10 so as to allow monitoring and control of the combustion for each grid 11.

Figure 7:
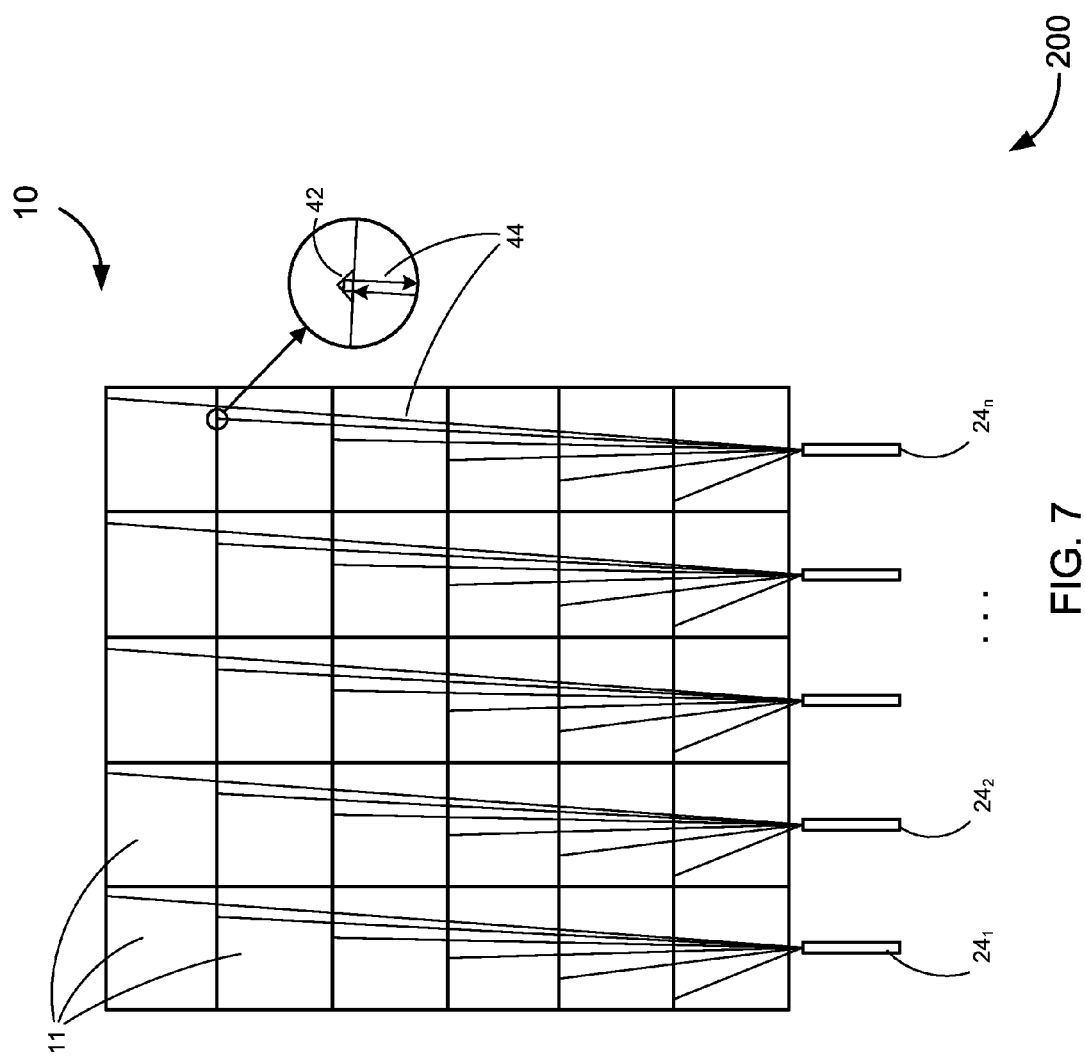
FIG. 7 is a top-view schematic illustration of an embodiment of a steerable tunable diode laser absorption spectroscopy system with a combination pitch/catch optic used in conjunction with an array of in-furnace retro-reflectors.

Alternatively, with respect to FIG. 7, an embodiment 200 may utilize the steering and "jumping" technique as described above to "jump" the beam 44 from one transmit and receive optic $24_x$ to a plurality of in-furnace retro-reflectors 42, which may be arranged in a single plane, in multiple planes, in a predetermined pattern, or in arbitrary positions within the furnace 10 (as described above). In one embodiment, as illustrated in FIG. 7, 5 transmit and receive optics $24_{1\text{-}to\text{-}n}$ may be used to monitor and control the combustion process in a 30-grid furnace, in which each grid 11 has positioned therein one of the 30 retro-reflectors 42.

Figure 8:
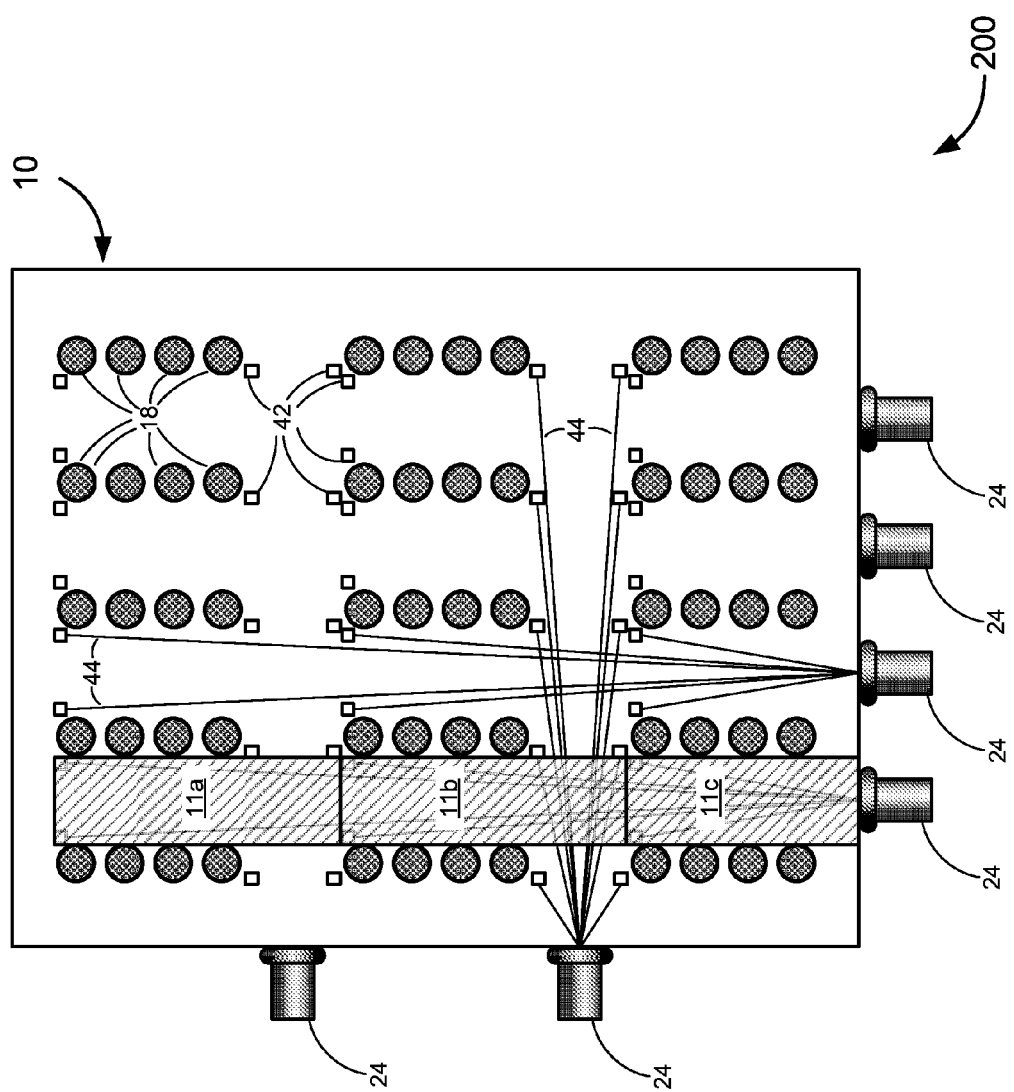
FIG. 8 is a plan-view schematic illustration of an embodiment of a steerable tunable diode laser absorption spectroscopy system with a combination pitch/catch optic used in conjunction with an array of in-furnace retro-reflectors, where combustion monitoring and control are performed on predetermined zones within the furnace.
Figure 11:
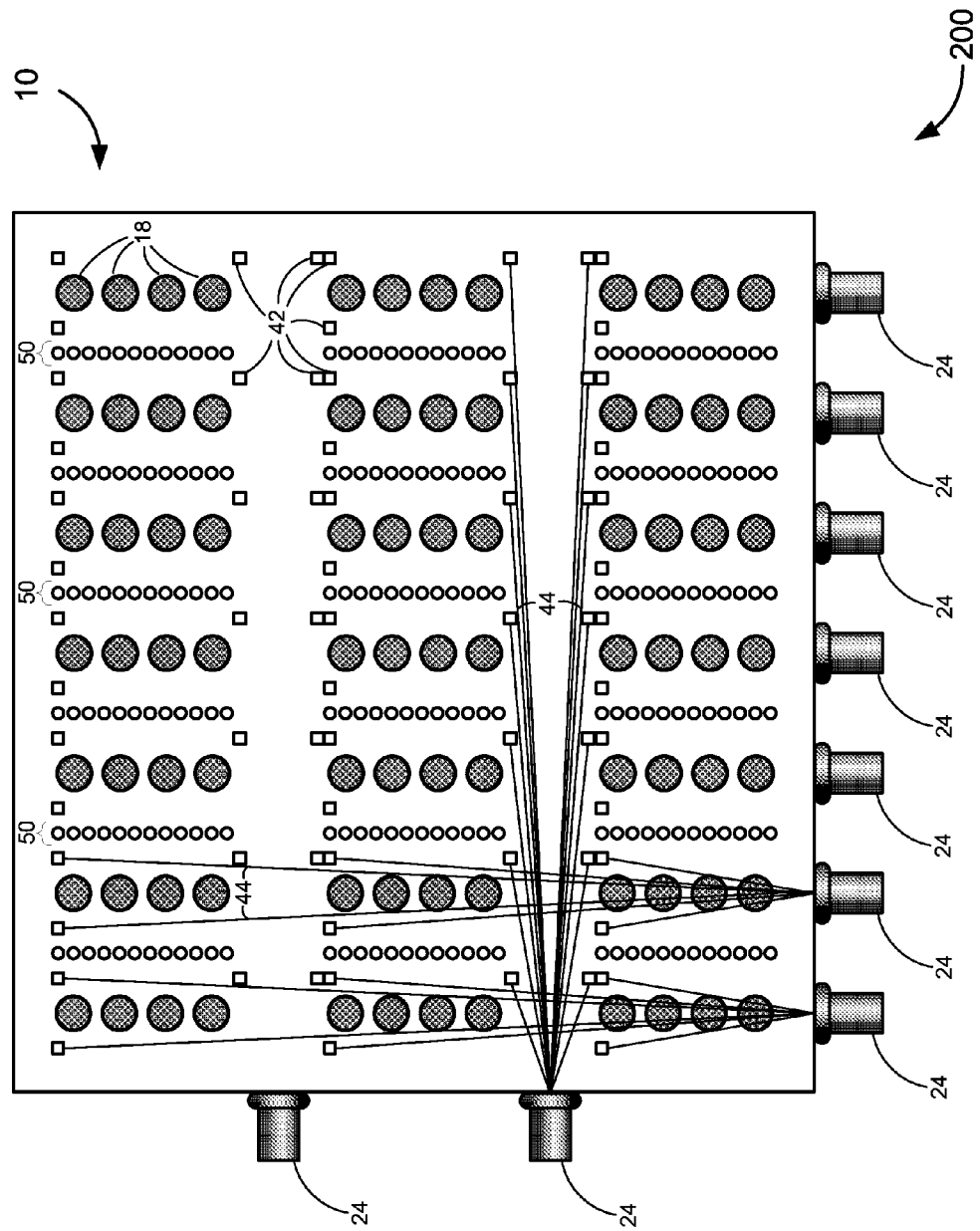
FIG. 11 is a plan view of a furnace with rows of process tubes between rows of burners showing a steerable tunable diode laser absorption spectroscopy system with a combination pitch/catch optic used in conjunction with an array of in-furnace retro-reflectors, where combustion monitoring and control are performed on predetermined zones within the furnace.

With reference to FIG. 8, an embodiment is shown wherein a plurality of transmit and receive optics 24 (which are each part of a steering and alignment system 20, e.g., as shown and described with respect to FIGS. 2A-5) are arranged about half of the perimeter of furnace 10 (e.g., along two walls 12 of a rectangular furnace 10 (as shown, e.g., in FIG. 8) or along an arc of a circular or elliptical furnace (not shown)). In some embodiments, retro-reflectors 42 are positioned in zones or grids 11 among burners 18. Embodiments of furnaces wherein the system could be use could include rows of process tubes 50 between the burners 18, for example as is known in Steam Methane Reformer (SMR) furnaces or other similarly designed furnaces with furnace tubes for performing other processes, such as ethylene cracking. A schematic plan view of such a furnace is show in FIG. 11. The retro-reflectors are positioned to allow sampling of the combustion zone downstream of a burner or appropriate groupings of burners and adjacent to the process tubes. Each transmit and receive optic 24 is configured to steer and "jump" its beam 44 to each of the retro-reflectors 42 in its assigned zones or grids 11.

In some embodiments, with reference with FIG. 8, the temperature or species concentration is measured along the shortest paths first corresponding to zone 11c. In such a case, transmit and receive optic 24 steers or "jumps" beam 44 to each of the two retro-reflectors 42 in zone or grid 11c. Once conditions are known in zone 11c, the beam 44 can be directed to retro-reflectors 42 that also enable sampling in zone 11b. With knowledge of the zone 11c conditions and the absorption measurements including those in zones 11c and 11b, the conditions can be calculated for zone 11b. Once conditions in zones 11b and 11c are known, zone 11a conditions can be measured in a similar fashion by directing the measurement beam 44 to retro-reflectors that enable sampling of zones 11a, 11b, and 11c. This process can be repeated for as many zones as is practical. Steering or "jumping" of beam 44 may be in any predetermined order, not necessarily from grid 11c to grid 11b to grid 11a. In such a case, the calculations of the zone conditions may be performed after all the measurements are made. The steering or "jumping" of beam 44 by each of the other transmit and receive optics 24 may be performed in a similar manner.

One benefit of this steering or "jumping" approach is that the number of furnace penetrations required decreases by at least a factor of 2; thereby decreasing installation costs. In addition, a single head may make measurements in a single plane as depicted in FIG. 8 or to locations that are not in the plane defined in FIG. 7. Thus, volumetric spatial information can be obtained.

Figure 9:
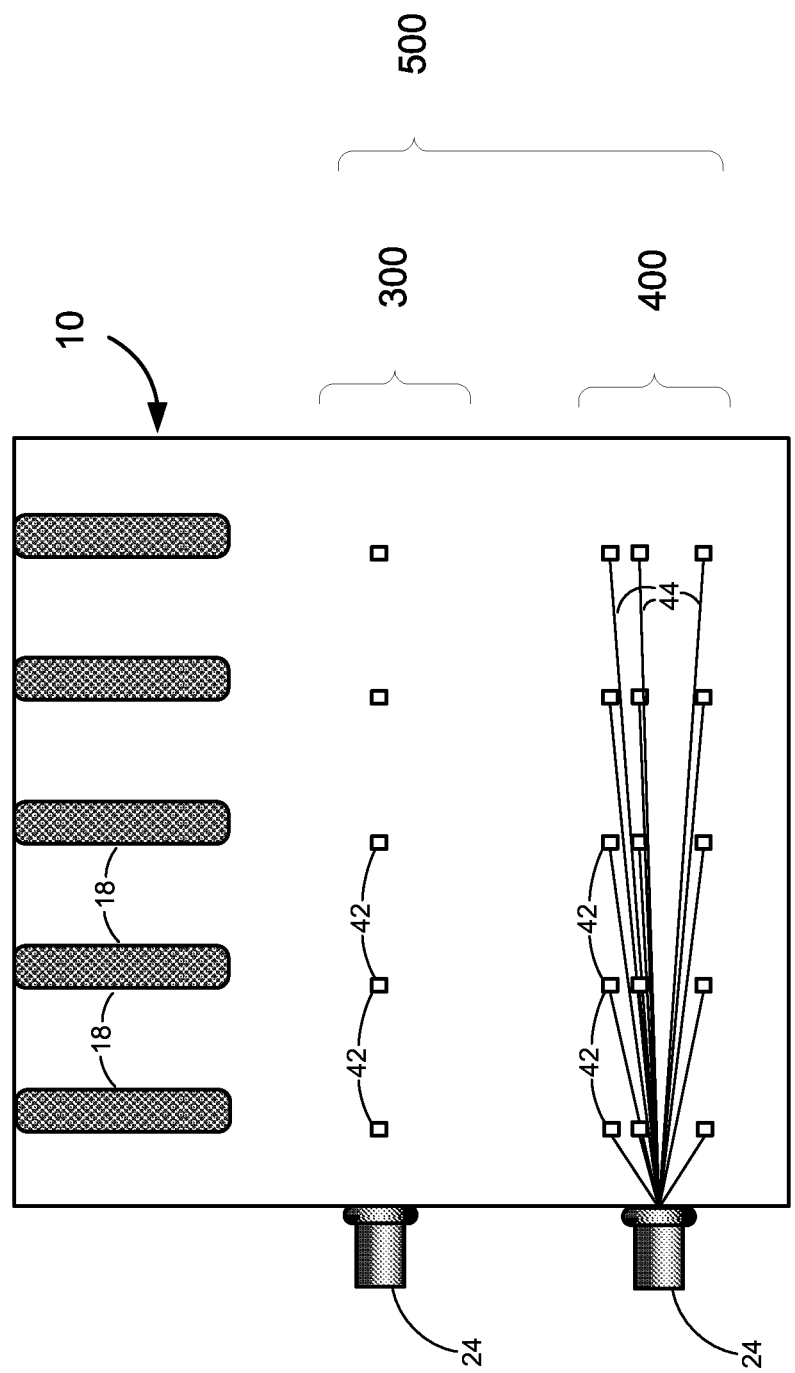
FIG. 9 is a side-view schematic illustration of an embodiment of a steerable tunable diode laser absorption spectroscopy system, where embodiment 300 illustrates (in-plane) 1D steerable monitoring, while embodiment 400 illustrates 2D steerable monitoring, and embodiment 500 illustrates multi-plane steerable monitoring.

FIG. 9 illustrates various embodiments for monitoring and controlling combustion in a furnace 10, including (in-plane) 1D steerable monitoring as shown in embodiment 300, 2D steerable monitoring as shown in embodiment 400, and multi-plane steerable monitoring as shown in embodiment 500. Herein, 1D and 2D refers to the dimensional steering from the perspective of the transmit and receive optics 24. For embodiments 300 and 400, the transmit and receive optics 24 may be arranged at any desirable height with respect to a floor of the furnace 10, and may be arranged about the sides of the furnace 10 in a similar manner as, e.g., shown in FIG. 8. For embodiment 500, any combination of 1D steerable monitoring and/or 2D steerable monitoring may be arranged about the furnace 10 (e.g., only 1D steerable monitoring arranged to monitor two or more parallel planes at two or more predetermined heights with respect to the floor of furnace 10; or 2D steerable monitoring arranged to monitor different height zones of furnace 10 with retro-reflectors arranged throughout substantially all or a portion of the interior of furnace 10; etc.). Although FIG. 9 depicts a downward-directed set of burners 18, which would emit flames downward to the floor of the furnace 10, the various embodiments are not so limited, and the burners 18 may be positioned in any location of the interior of the furnace—including on the floor of the furnace 10 with flames emitted toward the ceiling of the furnace 10, and on the side of the furnace 10 with flames emitted toward an opposite side of the furnace 10. In some cases, radiant wall burners may be used in which case flames are directed along the refractory lined furnace walls by burners mounted on these same walls. The purpose of these burners is to heat the refractory which then heats the tubes primarily by radiated heat transfer. In all such cases, the retro-reflectors would preferably be arranged generally down-flame of the burners 18 to the extent possible (e.g., on the opposite side of the furnace with respect to the burners) in the various possible configurations as described above or in any configuration that allows for monitoring and control of the combustion process in furnace 10.

Advantages of the use of retro-reflectors 42 include that fewer paths are required, thus avoiding complexities of angled paths in a tightly packed furnace. In addition, the laser beam 44 used to measure each cell must propagate out and back, thereby doubling the path length ("double-pass laser path") and increasing absorption signal strength. Stronger absorption signal reduces the deleterious effects of noise sources, such as modal, etalon, and detector noise. Further, "self-aligned laser paths" may be obtained. In other words, by definition, retro-reflecting targets in the furnace redirect the incident laser light back towards the source, where the sensor head collects the return light and sends it on to optical detectors. The sensor head needs to direct the transmitted beam towards the retro-reflector, but after that, no additional alignment is required. The auto-alignment process discussed above would be to align the beam with one of the retro-reflectors.

For effective use within a furnace, which can generally reach temperatures of 1000 to 1300° C. near the furnace gas exit, in-furnace retro-reflectors must be able to withstand these high temperatures, as well as being able to withstand an oxidizing environment. Not only does one need an optical element that can survive within that environment, one likely needs mounting or superstructure elements to hold the optical element in place.

Two potential materials that may be suitable for in-furnace retro-reflectors include sapphire, which has a melting point of 2030° C., and quartz, which has a melting point of 1670-1713° C. Thus, both sapphire and quartz can withstand the high temperatures of the furnace. As oxides, both sapphire and quartz are stable in oxidizing environments. Other materials may also work, but may be subject to cost and availability issues.

Aside from the materials for the retro-reflectors, there are various types to consider. For example, in some embodiments, a corner cube retro-reflector—a classic retro-reflector element—may be used. Corner cubes made of standard optical materials, including sapphire, are widely commercially available. The corner cube takes advantage of total internal reflection at the back side of the element so that its back reflection efficiency is very high. A corner cube has no optical power, so a diverging beam entering the cube exits as a beam with the same divergence. Thus, the highest retro-reflection efficiency back to the source occurs when the beam incident on the corner cube is collimated (plane wave illumination).

In another embodiment, a cat's eye retro-reflecting sphere may be used. A sphere with index of refraction 2.0 also retro-reflects an incident beam. The rays from a collimated illumination beam form a focus spot on the back surface of the sphere, where a portion of those rays reflects back along the same angle as the incident ray. Optical quality spheres generally cost less than a comparably sized retro-reflector.

One disadvantage of the cat's eye retro-reflector is lower overall reflectivity compared to that of a corner cube. Unlike in a corner cube, light bouncing off the back surface of the cat's eye is not totally internally reflected. The reflectivity of the back surface of the cat's eye depends on the index of refraction of the material but will be in the range of 4-8%. In lower temperature applications, according to some embodiments, partially reflective coatings, such as gold, may be applied to the sphere to increase its back reflectance.

According to some embodiments, rather than a single, large retro-reflector positioned at a particular location in the interior of the furnace, an array of smaller retro-reflectors may be used. An array of retro-reflectors 42' for retro-reflecting a single beam 44 will tend to act more like a phase conjugate mirror. That is, regardless of whether the illuminating beam is collimated, diverging, or converging, the retro-reflected beam will tend to retrace its incident path back to the source. So, a diverging source beam will be retro-reflected as a beam converging back towards the source. Furthermore, the smaller retro-reflecting elements will contribute to more scattering on reflection. Moreover, each retro-reflector element will produce an interference pattern on the reflected beam. This interference pattern would be observed as intensity fringes in the wavelength-scanned TDLAS signal. A single, large retro-reflector would be expected to have large, well-defined fringes because the number of interfering waves would be small. An array of small retro-reflectors, on the other hand, would produce many more interfering waves, and the resultant fringes in the TDLAS signal would likely be of smaller amplitude, be less stationary in time, and be easier to eliminate through signal averaging and mode scrambling. In addition, for a fixed retro-reflector surface area, an array of smaller elements may cost less than a single, large element.

In some embodiments, instead of each of discrete retro-reflectors or array retro-reflectors being positioned at discrete locations within the furnace for which one may desire to monitor and/or control combustion processes, one or more spanning retro-reflecting surfaces comprising an array of discrete small retro-reflector elements may be used where two or more retro-reflecting surfaces of each spanning retro-reflecting surface may cover a first location, a second location, a third location, and so on, in the furnace for which one may desire to monitor and/or control combustion processes. For such spanning retro-reflecting surfaces, the kinematic stage would be configured so as to "jump" the beam from one retro-reflecting surface located at the first location to another retro-reflecting surface located at the second location, and so on.

With regard to mounting of the retro-reflectors, according to some embodiments, a mounting superstructure may be used. For the mounting superstructure, ceramics are probably the best material as they can withstand both the high temperatures and the oxidizing environment. Ceramics may be machined or molded and fired to the desired shape. A ceramic superstructure could be formed with slots or other features to capture and hold retro-reflector optics. Although adhesives will not withstand furnace temperatures, sapphire or quartz optics may be fused to a ceramic mounting structure, according to one embodiment. Alternatively, according to another embodiment, optics could be captured/held in slots or other features formed into the ceramics.

Figure 12:
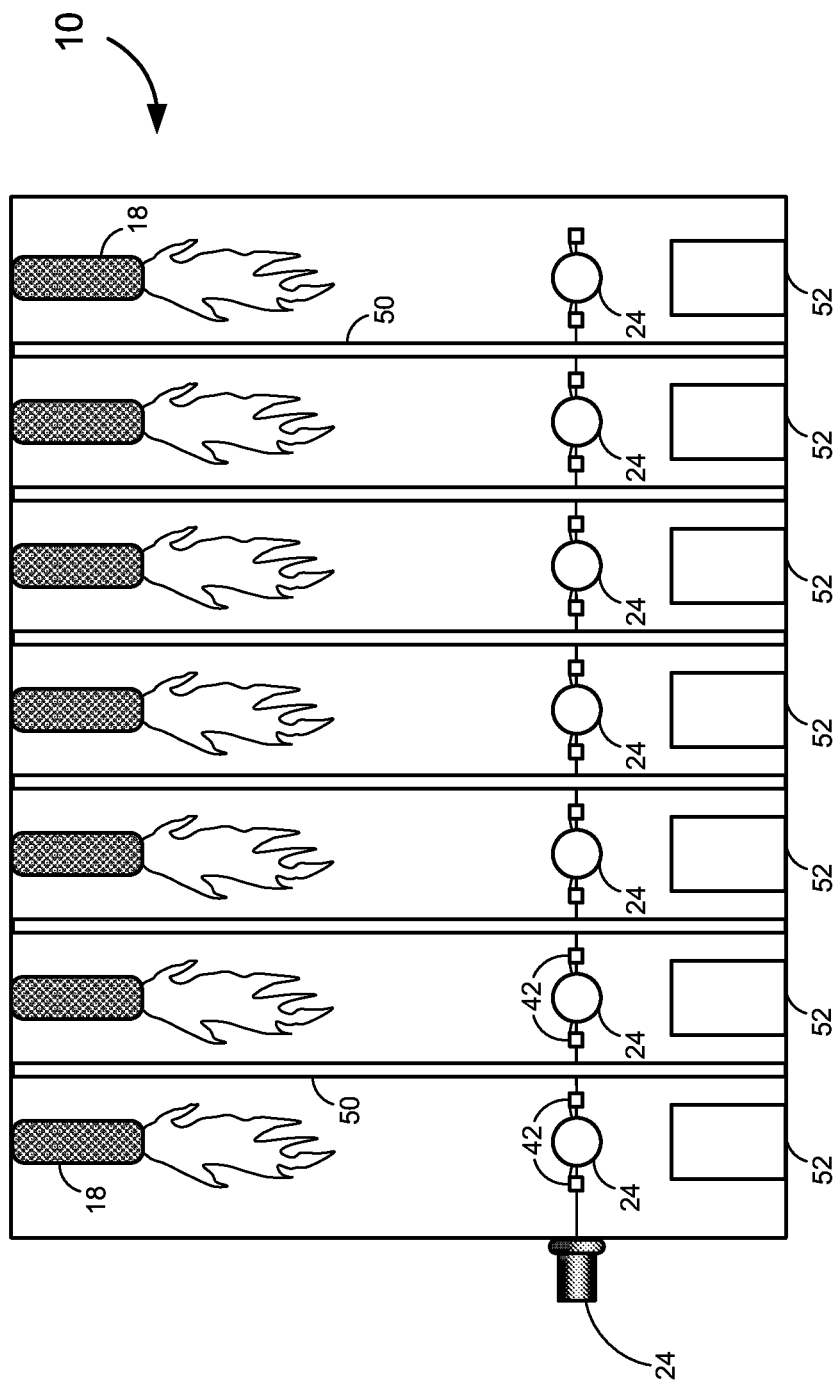
FIG. 12 is side view of down-fired furnace where the flue gas exits are located at the bottom of the furnace, further showing a steerable tunable diode laser absorption spectroscopy system with a combination pitch/catch optic used in conjunction with an array of in-furnace retro-reflectors, where combustion monitoring and control are performed on predetermined zones within the furnace.

Alternatively, according to one embodiment, nichrome wire may be used. A common nichrome alloy includes 80% nickel and 20% chromium, has a melting point of approximately 1400° C., and is relatively oxidation resistant due to a protective layer of chromium oxide. In one embodiment, arrays of retro-reflecting optics are wired together through holes in the optics (like beads on a string) or by creating wire cages to capture each element. The nichrome wire could then be tied into mounting features on the furnace or to the ceramic mounts. For down-fired furnaces, according to some embodiments, where the flue gas exits 52 are located at the bottom of the furnace (see FIG. 12), a hold-down feature, such as a ceramic pin that fits into a corresponding hole in the floor, is provided to mount the retro-reflectors on the bottom or floor of the furnace. Generally, since it is desirable to locate the laser paths where combustion is just complete, this arrangement would work well. In alternative embodiments, where up-fired or side-fired furnaces are used, the retro-reflector mounts may be located opposite the burners, where the flue gas exits are typically located, so that the laser paths are located where combustion is just complete. In the case of radiant wall burners, where the combustion is complete very close to the wall on which the burners are mounted since the flames are directed radially outward in a direction parallel to the wall, a gird may be close-coupled to the burner wall.

Figure 10:
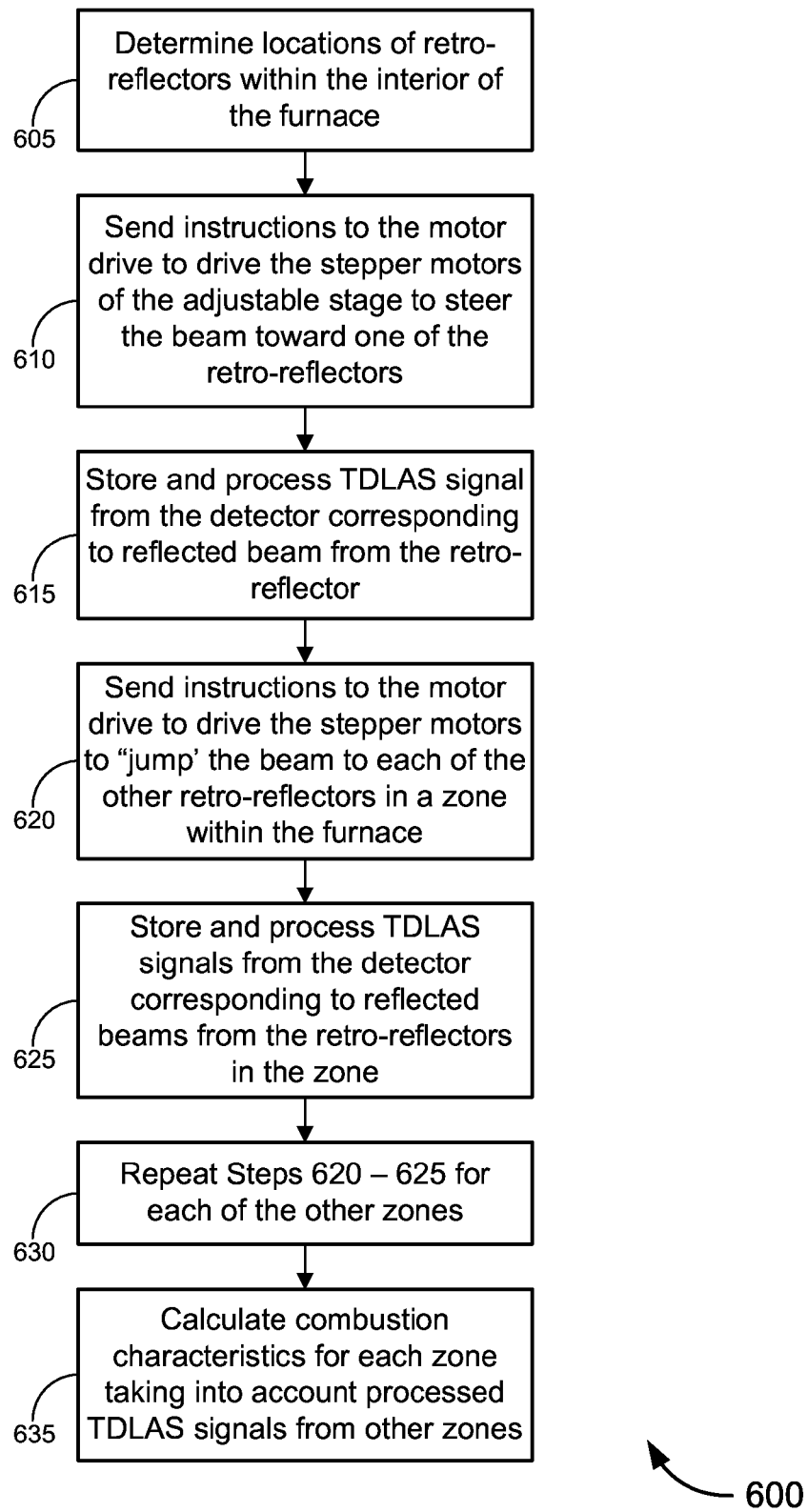
FIG. 10 is a flowchart illustrating zone-based monitoring and measurement of combustion properties within the interior of the furnace.

With reference to FIG. 10, a flowchart is shown illustrating an embodiment 600 for monitoring and calculating combustion properties for zones within the interior of the furnace. In Step 605, a general purpose or application specific computer may be used to determine the location of all the retro-reflectors positioned within the interior of a particular furnace. This may be accomplished, for example, by accessing a database on which is stored the locations of the retro-reflectors. Alternatively, a scanning beam could be used to scan the interior of the furnace, where the location of a retro-reflector is determined when a reflected beam (e.g., a back-reflected beam or a beam reflected to a separate detector) is detected. In Step 610, the computer sends instructions to the motor drive 26c to drive stepper motors 26b to tilt stage 26a so as to "steer" the beam to one of the retro-reflectors 42 (either a single, large retro-reflector or an array of smaller retro-reflecting elements). Auto-alignment, as described above, may be performed in order to ensure an optimal signal reflected from the retro-reflector 42. In Step 615, the computer stores and processes the TDLAS signal from the detector corresponding to the reflected beam from the retro-reflector 42. In Step 620, the computer sends instructions to the motor drive 26c to drive the stepper motors 26b to tilt stage 26a so as to "jump" the beam to each of the other retro-reflectors 42 in a predetermined zone of the furnace. Auto-alignment may also be performed at this time. In Step 625, the computer stores and processes the TDLAS signals from the detector corresponding to the reflected beam from all the retro-reflectors 42 in the zone.

In Step 630, Steps 620-625 are repeated for each of the other zones for which this particular transmit/receive optic is assigned. In Step 635, the computer calculates the combustion characteristics for each zone taking into account the calculations for other zones, in a manner similar to that described above with respect to FIG. 8. Steps 605-635 may subsequently be repeated for each transmit/receive optic. Software for controlling the computer may be stored on any recordable medium including, but not limited to, a floppy disk, a flash memory drive, a database, a server, an SD memory drive, a hard drive, etc.

Hereinabove, although typical retro-reflectors (including, but not limited to, corner cube, cat's eye, or other types of retro-retroflectors, etc.) may be used in the furnaces, optical mirrors or arrays or small optical mirrors may also be used to reflect the beam either back to the source optic or to a different optic mounted on the exterior of the wall of the furnace. However, such embodiments may be more difficult align a transmitted beam to be directed off the mirrors to the receiving optic than embodiments using a single transmit/receive optic and retro-reflectors.

Various embodiments of the disclosure could also include permutations of the various elements recited in the claims as if each dependent claim was multiple dependent claims incorporating the limitations of each of the preceding dependent claims as well as the independent claims. Such permutations are expressly within the scope of this disclosure.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

What is claimed is:

1. A method of monitoring combustion properties in an interior of a combustion furnace, the method comprising:
   providing at least one penetration in a wall of the furnace;
   providing at least two retro-reflecting surfaces within an interior of the furnace;
   projecting a beam of light through an optic comprising a collimating lens residing outside the interior of the furnace, the collimating lens being optically coupled to the at least one penetration to project the beam into the interior of the furnace toward a first retro-reflecting surface of the at least two retro-reflecting surfaces;

receiving the beam of light from the first retro-reflecting surface with the optic;

measuring the combustion properties based on the received beam of light from the first retro-reflecting surface;

steering the beam of light through the optic to a second retro-reflecting surface of the at least two retro-reflecting surfaces;

receiving the beam of light from the second retro-reflecting surface with the optic; and measuring the combustion properties based on at least the received beam of light from the second retro-reflecting surface.

2. The method of claim 1, wherein each of the at least two retro-reflecting surfaces is at least one of a single, large retro-reflector or an array of smaller retro-reflector elements.

3. The method of claim 1, wherein the first retro-reflecting surface and the second retro-reflecting surface are first and second portions of a single retro-reflecting surface comprising an array of discrete retro-reflectors, and wherein steering from the first retro-reflecting surface to the second retro-reflecting surface is steering from the first portion to the second portion of the single retro-reflecting surface.

4. The method of claim 1, wherein providing the at least two retro-reflecting surfaces within the interior of the furnace includes arranging a plurality of retro-reflectors in at least one of a single-plane configuration, a multi-plane configuration, a pre-arranged configuration, and an arbitrary configuration throughout the interior of the furnace.

5. The method of claim 4, wherein each plane of the single-plane configuration and the multi-plane configuration is either perpendicular to the wall of the furnace or parallel to the beam of light projected through the optic.

6. The method of claim 1, wherein steering the beam of light through the optic includes tilting the optic about at least one of two orthogonal axes that are perpendicular to an optical axis of the at least one penetration.

7. The method of claim 1, wherein receiving the beam of light includes receiving the beam in a multimode optical fiber, and wherein measuring the combustion properties includes filtering noise by averaging modal noise induced signal level variation of light propagating within the multimode optical fiber.

8. The method of claim 1, wherein providing the at least two retro-reflecting surfaces includes providing a plurality of retro-reflectors positioned within the interior of the furnace to monitor combustion zones within the furnace, wherein projecting the beam of light includes projecting the beam toward each of the plurality of retro-reflectors, and wherein measuring the combustion properties includes calculating the combustion properties by taking into account measurements of the beam reflected and received from each zone.

9. An apparatus for sensing combustion properties in an interior of a combustion furnace, the apparatus comprising:

a diode laser having a select lasing frequency;

a collimating lens optically coupled to a beam generated by the diode laser, the collimating lens being configured to project the beam from the diode laser into a penetration in a wall of the furnace;

at least two retro-reflecting surfaces positioned within an interior of the furnace, and each configured to reflect the beam from the collimating lens back to the collimating lens;

a kinematic tilt stage including at least one stepper motor, a motor drive, and a stage coupled to at least the collimating lens, wherein the at least one stepper motor is configured to tilt the stage about at least one of two orthogonal axes that are perpendicular to an optical axis of the first penetration, so as to steer the beam from a first retro-reflecting surface to a second retro-reflecting surface of the at least two retro-reflecting surfaces; and a detector sensitive to the select lasing frequency optically coupled to the collimating lens.

10. The apparatus of claim 9, wherein each of the at least two retro-reflecting surfaces is made of a material selected from the group consisting of sapphire and quartz.

11. The apparatus of claim 10, wherein each of the at least two retro-reflecting surfaces is one of a single, large retro-reflector and an array of smaller retro-reflector elements.

12. The apparatus of claim 10, wherein the at least two retro-reflecting surfaces includes at least one of a corner cube retro-reflecting optic and a cat's eye retro-reflecting sphere.

13. The apparatus of claim 9, further comprising a mounting structure provided within the interior of the furnace positioned on a side of the furnace opposite to a side of the interior of the furnace on which flame-emitting burners are located, wherein each of the at least two retro-reflecting surfaces is configured to be secured to a mounting structure.

14. The apparatus of claim 13, wherein the at least one mounting structure includes a ceramic mounting structure having slots in which each of the retro-reflecting surfaces is held.

15. The apparatus of claim 13, wherein the furnace includes a ceiling and a floor, the ceiling and floor are substantially perpendicular to the wall of the furnace, and wherein the flame-emitting burners are mounted to the ceiling, while the mounting structures are mounted to the floor.

16. The apparatus of claim 9, wherein the at least two retro-reflecting surfaces includes a plurality of retro-reflectors arranged in at least one of a single-plane configuration, a multi-plane configuration, a pre-arranged configuration, and an arbitrary configuration throughout the interior of the furnace.

17. The apparatus of claim 16, wherein each plane of the single-plane configuration and the multi-plane configuration is either perpendicular to the wall of the furnace or parallel to the beam projected through the optic.

18. The apparatus of claim 9, further comprising a multimode optical fiber optically coupled to the collimating lens and the detector, and configured to receive the reflected beam from the collimating lens and to transmit the reflected beam to the detector.

19. The apparatus of claim 18, further comprising a noise reduction component that is configured to filter noise by averaging modal noise induced signal level variation of light propagating within the multimode optical fiber, and to output a filtered signal to the detector.

20. The apparatus of claim 9, further comprising a relay lens optically coupled to the collimating lens and the penetration, the relay lens being configured to project the beam from the diode laser, through the collimating lens and the penetration, to the at least two retro-reflecting surfaces, and to receive the reflected beam from each of the at least two retro-reflecting surfaces and transmit the reflected beam to the detector.

* * * * *